(12) United States Patent
Alagramam

(10) Patent No.: US 11,827,680 B2
(45) Date of Patent: Nov. 28, 2023

(54) COMPOUNDS AND METHODS OF TREATING USHER SYNDROME III

(71) Applicant: Case Western Reserve University, Cleveland, OH (US)

(72) Inventor: Kumar N. Alagramam, Cleveland, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 728 days.

(21) Appl. No.: 15/525,270

(22) PCT Filed: Nov. 6, 2015

(86) PCT No.: PCT/US2015/059546
§ 371 (c)(1),
(2) Date: May 8, 2017

(87) PCT Pub. No.: WO2016/073900
PCT Pub. Date: May 12, 2016

(65) Prior Publication Data
US 2018/0282382 A1 Oct. 4, 2018

Related U.S. Application Data

(60) Provisional application No. 62/158,846, filed on May 8, 2015, provisional application No. 62/076,114, filed on Nov. 6, 2014.

(51) Int. Cl.
A61K 48/00 (2006.01)
C12N 15/63 (2006.01)
C12N 15/86 (2006.01)
C07K 14/47 (2006.01)
A61K 31/7105 (2006.01)
A61K 31/711 (2006.01)
A61P 27/16 (2006.01)
A01K 67/00 (2006.01)

(52) U.S. Cl.
CPC ............ C07K 14/47 (2013.01); A61K 31/711 (2013.01); A61K 31/7105 (2013.01); A61P 27/16 (2018.01); C12N 15/86 (2013.01); A61K 48/00 (2013.01); C12N 2750/14143 (2013.01)

(58) Field of Classification Search
CPC .. A61K 48/00; A61K 31/7105; A61K 31/711; C12N 15/86; C12N 2750/14143; A61P 27/16
See application file for complete search history.

(56) References Cited

U.S. PATENT DOCUMENTS 9,061,059 B2 * 6/2015 Chakraborty et al.
9,783,545 B2 10/2017 Burli et al.
10,561,636 B2 2/2020 Alagramam et al.

2006/0051331 A1 3/2006 Mallet et al.
2011/0229971 A1 * 9/2011 Knop et al.
2013/0095071 A1 * 4/2013 Bance et al.

FOREIGN PATENT DOCUMENTS

WO 2003097685 A1 11/2003
WO 2012087983 A1 6/2012

OTHER PUBLICATIONS

Hanna E et al. Gene therapies development: slow progress and promising prospect. Journal of Market Access & Health Policy 5, 1265293; doi.org/10.1080/2016689.2017.1265293, pp. 1-9, (Year: 2017).*
Ramamoorth M et al. Non Viral Vectors in Gene Therapy—An Overview. Journal of Clinical and Diagnostic Research 9:GE01-GE06, (Year: 2015).*
Geng R et al. Modeling and preventing progressive hearing loss in Usher Syndrome III. Scientific Reports 7:13480; doi:10.1038/s41598-017-13620-9; pp. 1-15, (Year: 2017).*
Geng, et al., "Usher Syndrome IIIA Gene Clarin-1 is Essential for Hair Cell Function and Associated Neural Activation", Hum Mol Genet, May 3, 2009, vol. 18, No. 15, pp. 2748-2760.
Isosomppi, et al., "Disease-causing mutations in the CLRN1 Gene alter normal CLRN1 protein trafficking to the plasma membrane", Molecular Vision, Sep. 8, 2009, vol. 15, pp. 1806-1818.
Shearer, A. Eliot, et al., "Comprehensive genetic testing for hereditary hearing loss using massively parallel sequencing", PNAS, Dec. 7, 2010, vol. 107, No. 49.
Thorpe, Ryan K., et al., "Future directions for screening and treatment in congenital hearing loss", Precision Clinical Medicine, 0(0), 2020, 1-12. Jul. 16, 2020.
Alagramam, Kumar N., et al., "The mouse Ames waltzer hearing-loss mutant is caused by mutation of Pcdh 15, a novel protocadherin gene" Nature Genetics, vol. 27, Jan. 2001.
Alagramam, Kumar N., et al., "Mutations in Protocadherin 15 and Cadherin 23 Affect Tip Links and Mechanotransduction in Mammalian Sensory Hair Cells", Apr. 2011, vol. 6, Issue 4.
Alagramam, Kumar N., et al., "A small molecule mitigates hearing loss in a mouse model of Uusher syndrome III", Nature Chemical Biology, Apr. 25, 2016, ppg. 1-13.
Gopal, Suhasini, et al., "Unconventional secretory pathway activation restores hair cell mechanotransduction in an USH3A model", pnas, Apr. 17, 2019, PGG. 1-10.
Joensuu, Tarja, et al., Mutations in a Novel Gene with Transmembrane Domains Underlie Usher Syndrome Type 3, Am. J. Hum. Genet. 69:673-684, 2001.

(Continued)

Primary Examiner — Quang Nguyen
(74) Attorney, Agent, or Firm — TAROLLI, SUNDHEIM, COVELL & TUMMINO, LLP

(57) ABSTRACT

An isolated polynucleotide includes a nucleic acid sequence that includes a cDNA coding sequence of a clarin-1 gene and a 3'UTR nucleic acid that is derived from the 3'UTR of the clarin-1 gene. The 3'UTR nucleic acid can enhance expression of clarin-1 in a cell transfected with the polynucleotide compared to a cell transfected with a similar polynucleotide devoid of the 3'UTR nucleic acid.

4 Claims, 5 Drawing Sheets
Specification includes a Sequence Listing.

(56) References Cited

OTHER PUBLICATIONS

Adato, Avital, et al., "USH3A transcripts encode clarin-1, a fourtransmembrane-domain protein with a possible role in sensory synapses", European Journal of Human Genetics (2002) 10, 339-350.

Ness, S.L., et al., "Genetic homogeneity and phenotypic variability among Ashkenazi Jews with Usher syndrome type III", J Med Genet 2003;40:767-772.

Sadeghi, Mehdi, et al., "Audiological and vestibular features in affected subjects with USH3: A genotype/phenotype correlation", International Journal of Audiology 2005; 44:307-316.

Pakarinen, L., et al., "Usher's Syndrome Type 3 in Finland", Laryngoscope 105: Jun. 1995.

Smith, R.J.H., et al., "Clinical Diagnosis of the Usher Syndromes", American Journal of Medical Genetics 50:32-38 (1994).

\* cited by examiner

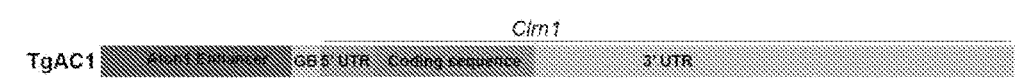
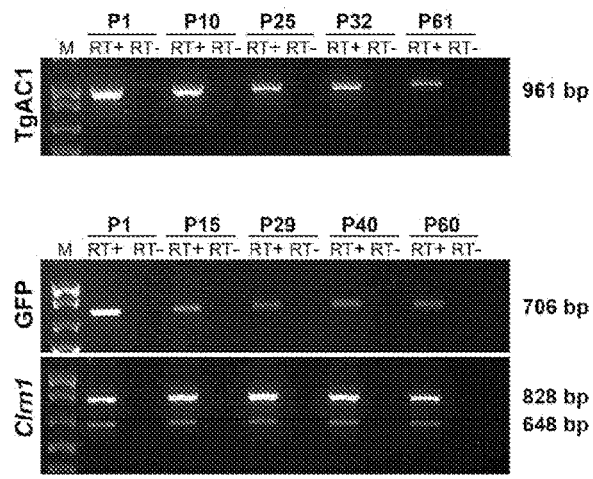
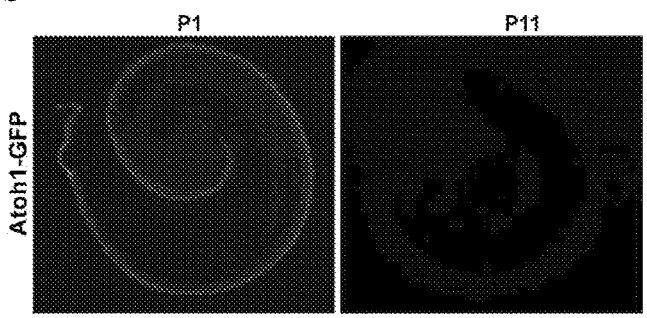
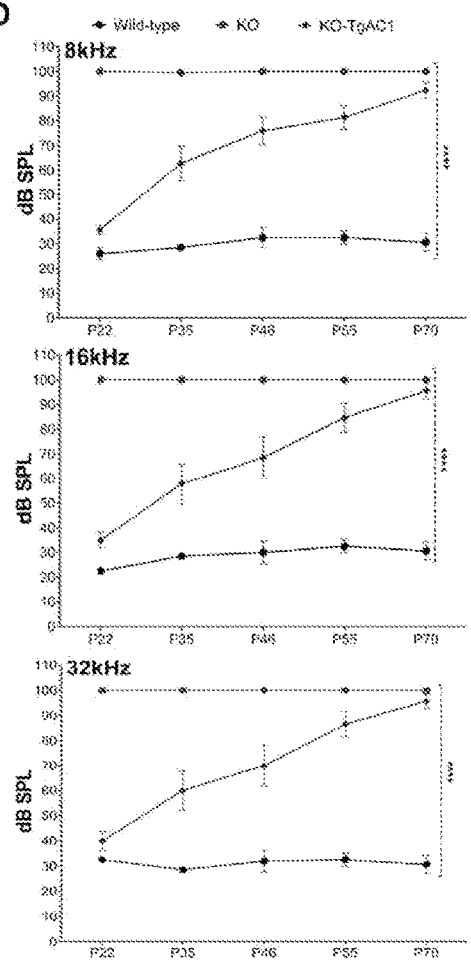
Figs. 1A-D

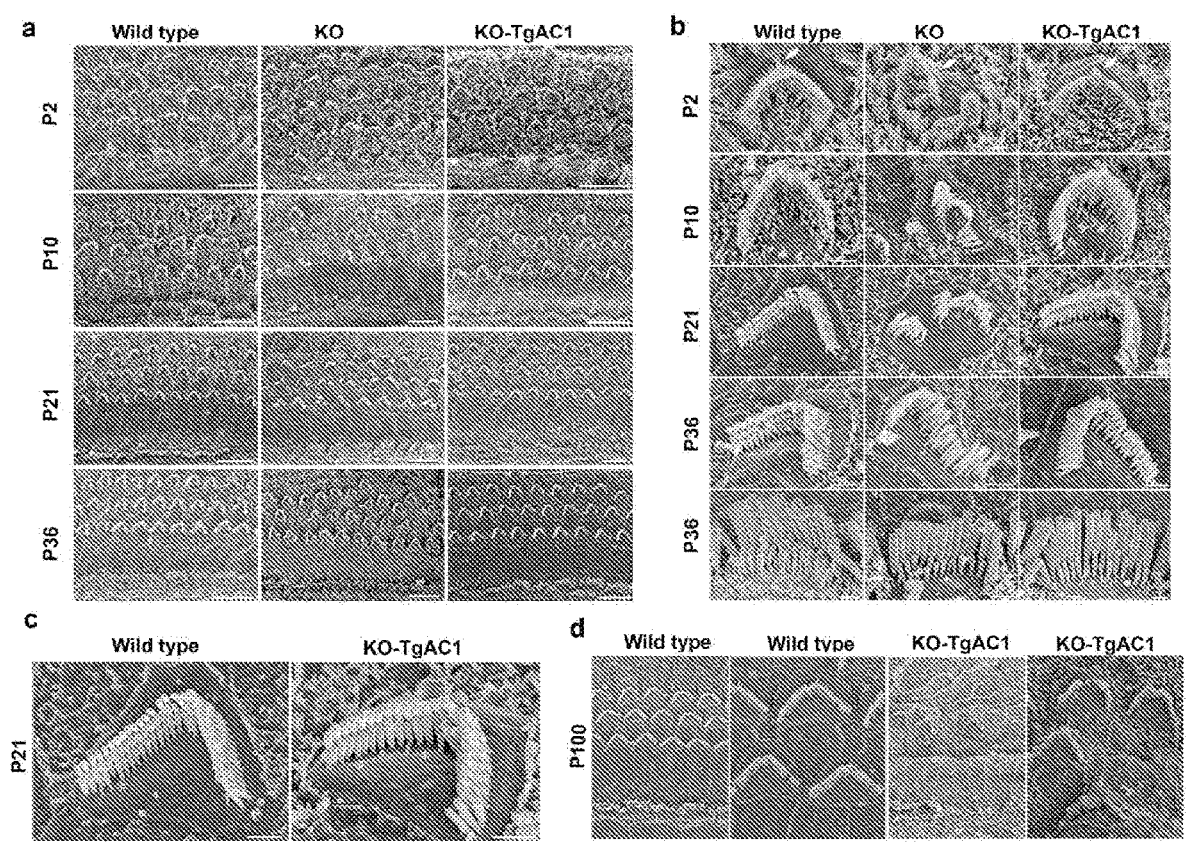
Figs. 2A-D

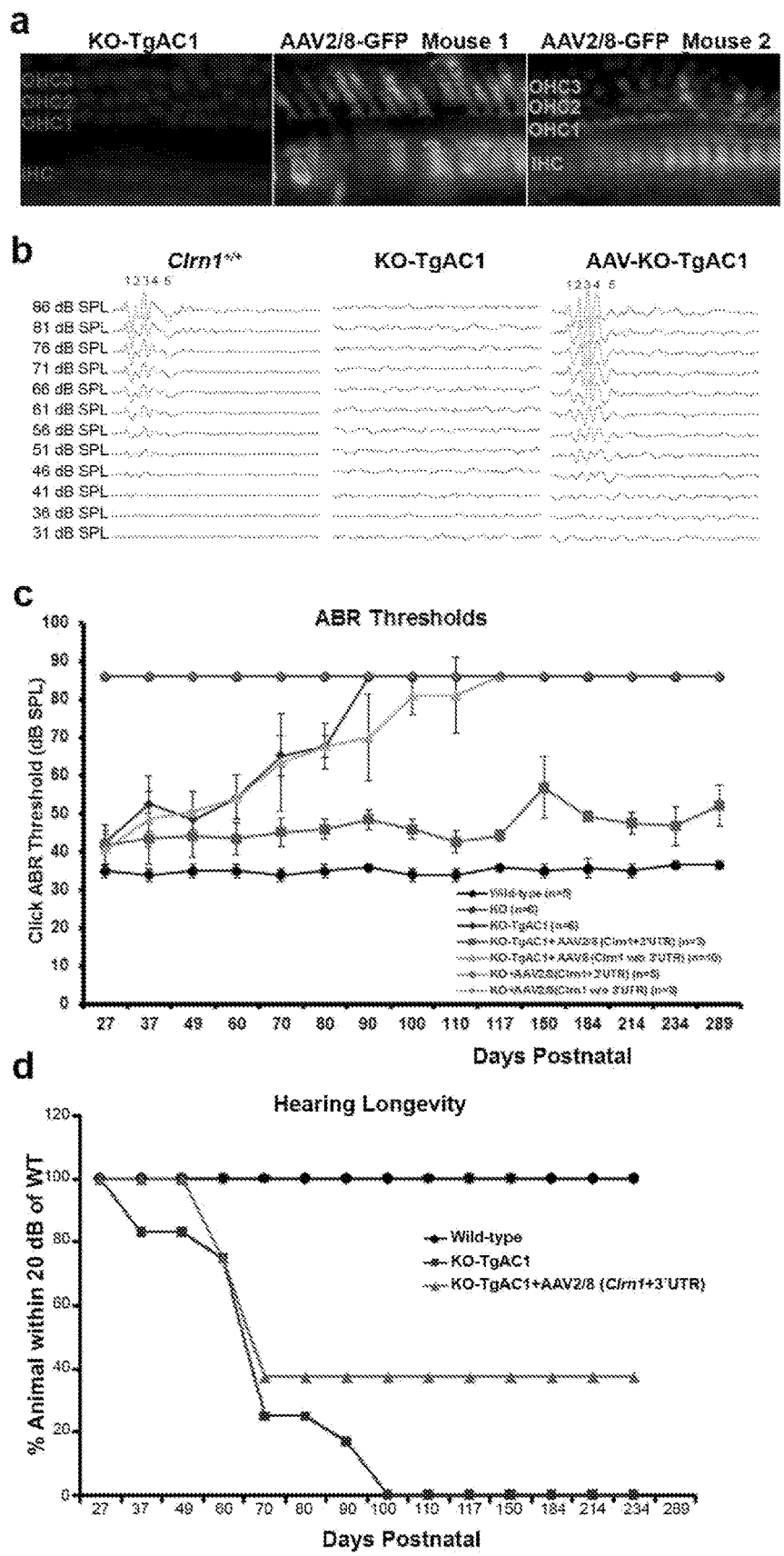
Figs. 3A-D

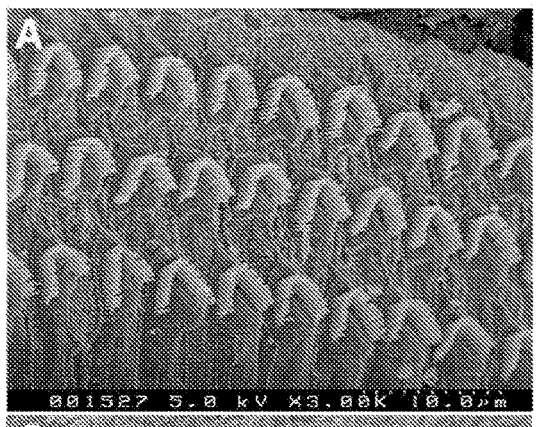
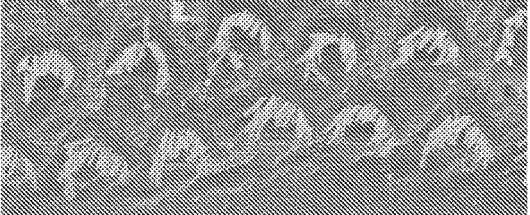
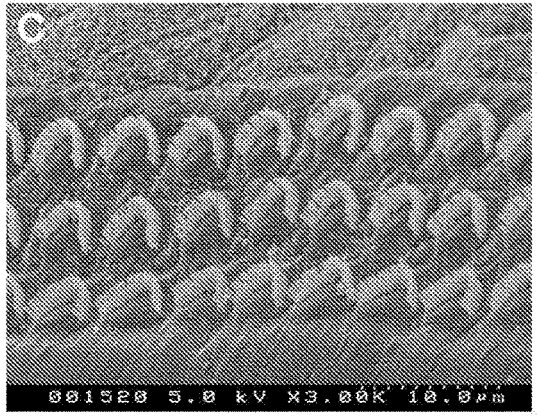
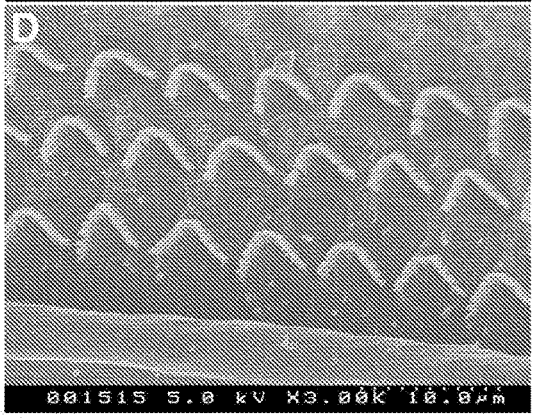
Figs. 4A-D

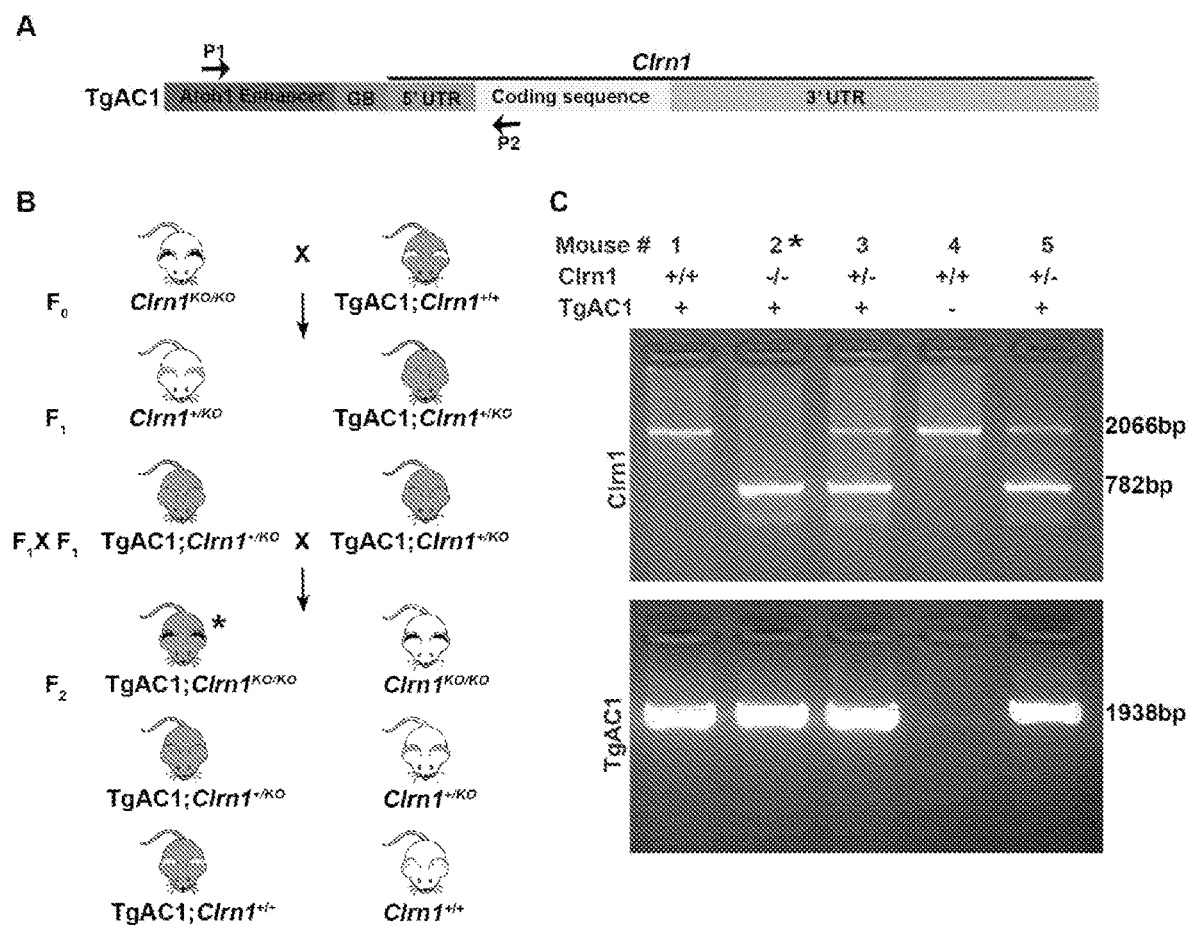
Figs. 5A-C

COMPOUNDS AND METHODS OF TREATING USHER SYNDROME III

RELATED APPLICATION

This application claims priority from U.S. Provisional Application Nos. 62/076,114, filed Nov. 6, 2014 and 62/158,846 filed May 8, 2015, the subject matter of which are incorporated herein by reference in their entirety.

GOVERNMENT FUNDING

This invention was made with government support under DC009246 awarded by the National Institutes of Health. The government has certain rights in the invention.

TECHNICAL FIELD

This application relates to compositions and methods of treating a subject having Usher syndrome III, and particularly relates to the use of a polynucleotide encoding Clarin-1 for the treatment of hearing and/or vision loss associated with Usher syndrome III.

BACKGROUND

Usher syndrome (USH) is the most common cause of sensory impairment wherein deafness and blindness occur together. It is clinically subdivided into three types based on the degree of deafness and the presence of vestibular dysfunction. USH type 1 (USH1) is the most severe form and is characterized by profound congenital hearing loss and vestibular dysfunction combined with pre-pubertal onset of retinitis pigmentosa (RP). In USH2, hearing loss is milder, the onset of RP is after puberty and vestibular function is unaffected. USH3 patients show progressive hearing loss and variable degrees of vestibular dysfunction. At least 13 loci have been linked to the three types of Usher syndrome, including one locus linked to USH3.

USH3 is caused by mutations in the clarin-1 (CLRN1) gene which encodes a four transmembrane protein (CLRN1) closely related to tetraspanins. $CLRN1^{Y176X}$ and $CLRN1^{N48K}$ are the most common mutation among USH3 cases. CLRN1 shares some of the features common to tetraspanin proteins, including the predicted four transmembrane domain topology, and very short intracellular loops. This protein may play a vital role in creating and assembling membrane microdomains involved in adhesion strengthening and signaling. However, the precise function of CLRN1 in the inner ear is not known. There is no treatment or cure for ear or eye disease in USHIII at this time.

SUMMARY

This application relates to compositions and methods of treating a subject having Usher syndrome III, and particularly relates to the use of a polynucleotide encoding Clarin-1 for the treatment of hearing and/or vision loss associated with Usher syndrome III (USH3).

In some embodiments, the composition can include an isolated polynucleotide comprising a nucleic acid sequence that includes a cDNA coding sequence of a clarin-1 gene and a 3'UTR nucleic acid that is derived from the 3'UTR of the clarin-1 gene. The 3'UTR nucleic acid can enhance expression of clarin-1 in a cell transfected with the polynucleotide compared to a cell transfected with a similar polynucleotide devoid of the 3'UTR nucleic acid.

In some embodiments, the clarin-1 cDNA can include wild-type clarin-1 cDNA. For example, the clarin-1 cDNA can have a sequence identity of SEQ ID NO: 3 or SEQ ID NO: 4. The nucleic acid sequence can further include the 5'-UTR of the clarin-1 gene or be devoid of the 5'-UTR of the clarin-1 gene.

In other embodiments, the 3'UTR nucleic acid can have at least about 70%, at least about 80%, at least about 90%, at least about 95%, or at least about 99% sequence identity to SEQ ID NO: 5 or SEQ ID NO: 6 and/or the 3'UTR nucleic acid can include at least about 100, at least about 500, at least about 1000, at least about 1500, or at least about 2000 consecutive nucleotides of SEQ ID NO: 5 or SEQ ID NO: 6.

In some embodiment, the isolated polynucleotide can include clarin-1 cDNA with the associated 5'UTR and 3'UTR. For example, the isolated polynucleotide can include a nucleic acid sequence having SEQ ID NO: 1 or SEQ 2.

In other embodiments, the polynucleotide can be included in a nucleic acid construct or vector that can be used for transfecting cells, such as ocular cells or cells of the inner ear. The transfected cells can express clarin-1 at amount effective to treat vision and/or hearing loss in the subject associated with USH3. In some embodiments, the vector can be an adeno-associated viral vector. Other embodiments relate to a method of treating vision and/or hearing loss associated with USH3 in a subject in need thereof by administering to ocular cells and/or cells of the inner ear of the subject a therapeutically effective amount of vector that promotes expression of clarin-1 in the cells. The vector can include an isolated polynucleotide comprising a nucleic acid sequence that includes a cDNA coding sequence of a clarin-1 gene and a 3'UTR nucleic acid that is derived from the 3'UTR of the clarin-1 gene. The 3'UTR nucleic acid can enhance expression of clarin-1 in the cells transfected with the polynucleotide compared to a cell transfected with a similar polynucleotide devoid of the 3'UTR nucleic acid.

In some embodiments, the cells are cells of the inner ear and the vector is administered at an amount effective to treat hearing loss in the subject. In other embodiments, the cells are retinal cells and the vector is administered at an amount effective to treat vision loss in the subject.

BRIEF DESCRIPTION OF THE DRAWINGS

FIGS. 1(A-D) illustrate: (A) Schematic diagram showing Atoh1-Clrn1 and Atoh1-GFP transgene constructs. (B) Expression analysis of Clrn1 and GFP mRNA from the cochlea of KO-TgAC1 or WT mice at various time points. (C) GFP expression in the organ of Corti at P1 and P11 from the Atoh1-GFP transgenic line. (D) ABR thresholds of wild-type, KO and KO-TgAC1 mice from P22 to P70 at 8, 16 and 32 kHz.

FIGS. 2(A-D) illustrate FESEM images of P2 wild type, knockout and rescue organ of Corti. The knockout shows some disturbance of the hair cell rows that is not visible in either wild type or rescue. At P10, the knockout is again more disturbed than the rescue and the wild type. Compared with the wild type, however, the knockout and rescue appear to have longer inner pillar cell heads (IPC). At P21 and P36 the normal regularity of the organ of Corti is evident in the rescue and wild type but not the knockout. Scale bars=10 µm.

FIGS. 3(A-D) illustrate: (A) AAV2/8-GFP transduction in the KO-TgAC1 mice organ of Corti. Representative specimens from mid-basal turn of the cochlea at P10 from 2 of the 5 mice injected with AAV2/8-GFP are shown here (middle and right panel). (B) Representative ABR tracings to click stimulus from Clrn1+/+, KO-TgAC1 and AAV-KO-TgAC1 (Clrn1-3' UTR). (C) Plots showing long term hearing preservation in KO-TgAC1 mice transfected with AAV2/8 Clrn1-3'UTR construct. (D) Plots showing hearing longevity, as defined as the number of mice with ABR threshold levels within 20 dB SPL of wild-type levels at each time point, is measured for all mice injected with the AAV2/8 Clrn1-3'UTR compared to the wild-type and the KO-TgAC1.

FIGS. 4(A-D) illustrate FESEM images of outer hair cells (OHC) of Organ of Corti from P100 mice. The mice include (A) wild type control; (B) knockout (KO)-TgAC1; and rescue (C) KO-TgAC1-AAV2-Clrn-UTR; and (D) rescue KO-TgAC1-AAV8-Clrn1-UTR.

FIGS. 5(A-C) illustrate: (A) A schematic of a transgene construct. The transgene construct is composed of regulatory element Atoh1 enhancer fused to beta globin basal (GB) promoter sequence. The Clrn1 cDNA fused downstream of the regulatory elements is composed 5'untranslated (UTR) sequence, coding sequence (isoform 2) and 3'UTR sequence. (B) The breeding scheme used to generate KO-TgAC1 mice. The expanded symbol for the KO-TgAC1 mice is "TgAC1; Clrn1KO/KO", marked by an asterisk in the F2 generation. (C) PCR-based genotyping to identify wild-type (2066 bp), knockout (782 bp) and TgAC1 (1938 bp) allele of Clrn1. Lane #2 (*) shows genotype of F2 mice with the desired genotype, TgAC1; Clrn1KO/KO.

DETAILED DESCRIPTION

It should be understood that the present invention is not limited to particular methods, reagents, compounds, compositions or biological systems, which can, of course, vary. It should also to be understood that the terminology used herein is for the purpose of describing particular aspects of the present invention only, and is not intended to be limiting. Unless defined otherwise, all technical and scientific terms used herein have the same meaning as commonly understood by one of ordinary skill in the art to which the present invention pertains. Although any methods and materials similar or equivalent to those described herein can be used in the practice of the present invention, the preferred materials and methods are described herein. In describing and claiming the present invention, the following terminology will be used.

Methods involving conventional molecular biology techniques are described herein. Such techniques are generally known in the art and are described in detail in methodology treatises, such as Current Protocols in Molecular Biology, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., Glossary of Genetics: Classical and Molecular, 5th Edition, Springer-Verlag: New York, 1991, and Lewin, Genes V, Oxford University Press: New York, 1994. The definitions provided herein are to facilitate understanding of certain terms used frequently herein and are not meant to limit the scope of the present invention.

"AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector"). The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc.

The genomic sequences of various serotypes of AAV, as well as the sequences of the native terminal repeats (TRs), Rep proteins, and capsid subunits are known in the art. Such sequences may be found in the literature or in public databases such as GenBank. See, e.g., GenBank Accession Numbers $NC\_{\_002077}$ (AAV-1), AF063497 (AAV-1), $NC\_{\_001401}$ (AAV-2), AF043303 (AAV-2), $NC\_{\_001729}$ (AAV-3), $NC\_{\_001829}$ (AAV-4), U89790 (AAV-4), $NC\_{\_006152}$ (AAV-5), AF513851 (AAV-7), AF513852 (AAV-8), and $NC\_{\_006261}$ (AAV-8); the disclosures of which are incorporated by reference herein for teaching AAV nucleic acid and amino acid sequences. See also, e.g., Srivistava et al. (1983) J. Virology 45:555; Chiorini et al. (1998) J. Virology 71:6823; Chiorini et al. (1999) J. Virology 73:1309; Bantel-Schaal et al. (1999) J. Virology 73:939; Xiao et al. (1999) J. Virology 73:3994; Muramatsu et al. (1996) Virology 221:208; Shade et al. (1986) J. Virol. 58:921; Gao et al. (2002) Proc. Nat. Acad. Sci. USA 99:11854; Moris et al. (2004) Virology 33:375-383; international patent publications WO 00/28061, WO 99/61601, WO 98/11244; and U.S. Pat. No. 6,156,303.

A "rAAV vector" refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two, AAV inverted terminal repeat sequences (ITRs). The term rAAV vector encompasses both rAAV vector particles and rAAV vector plasmids. A rAAV vector may either be single-stranded (ssAAV) or self-complementary (scAAV).

An "AAV virus" or "AAV viral particle" or "rAAV vector particle" refers to a viral particle composed of at least one AAV capsid protein (typically by all of the capsid proteins of a wild-type AAV) and an encapsidated polynucleotide rAAV vector. If the particle comprises a heterologous polynucleotide (i.e., a polynucleotide other than a wild-type AAV genome, such as a transgene to be delivered to a mammalian cell), it is typically referred to as a "rAAV vector particle" or simply a "rAAV vector". Thus, production of rAAV particle necessarily includes production of rAAV vector; as such a vector is contained within a rAAV particle.

The term "construct" or "nucleic acid construct" refers to a recombinant nucleotide sequence, generally a recombinant nucleic acid molecule or cDNA, that has been generated for the purpose of the expression of a specific nucleotide sequence(s), or is to be used in the construction of other recombinant nucleotide sequences.

The term "gene" refers to a nucleic acid comprising a nucleotide sequence that encodes a polypeptide or a biologically active ribonucleic acid (RNA), such as a tRNA, shRNA, miRNA, cDNA, etc. The nucleic acid can include regulatory elements (e.g., expression control sequences, such as promoters, enhancers, an internal ribosome entry site (IRES)) and/or introns. A "gene product" or "expression product" of a gene is an RNA transcribed from the gene (e.g., pre- or post-processing) or a polypeptide encoded by an RNA transcribed from the gene (e.g., pre- or post-modification).

The terms "gene of interest," "nucleotide sequence of interest" and "nucleic acid of interest" refer to any nucleotide or nucleic acid sequence that encodes a protein or other molecule that is desirable for expression in a host cell (e.g., for production of the protein or other biological molecule (e.g., an RNA product) in the target cell). The nucleotide sequence of interest is generally operatively linked to other sequences which are needed for its expression, e.g., a promoter. Further, the sequence itself may be regulatory in nature and thus of interest for expression of biologies in the target cell.

The term "gene therapy" refers to a treatment of a patient's body or isolated elements of a patient's body, for example isolated tissues/cells, by nucleic acids encoding a peptide or protein. It typically may comprise at least one of the steps of a) administration of a nucleic acid directly to the patient—by whatever administration route—or in vitro to isolated cells/tissues of the patient, which results in transfection of the patient's cells either in vivo, ex vivo, or in vitro, b) transcription and/or translation of the introduced nucleic acid molecule; and optionally c) re-administration of isolated, transfected cells to the patient, if the nucleic acid has not been administered directly to the patient.

An "isolated" plasmid, nucleic acid, vector, virus, virion, host cell, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. An isolated plasmid, nucleic acid, vector, virus, host cell, or other substance is in some embodiments purified, e.g., from about 80% to about 90% pure, at least about 90% pure, at least about 95% pure, at least about 98% pure, or at least about 99%, or more, pure.

The terms "nucleic acid" and "nucleic acid molecule" refer to polynucleotides, such as DNA or RNA. Nucleic acids can be single-stranded, partly or completely, double-stranded, and in some cases partly or completely triple-stranded. Nucleic acids include genomic DNA, cDNA, mRNA, etc. Nucleic acids can be purified from natural sources, produced using recombinant expression systems and optionally purified, chemically synthesized, e.g., iRNA, siRNAs, microRNAs, and ribonucleoproteins. Where appropriate, e.g., in the case of chemically synthesized molecules, nucleic acids can comprise nucleoside analogs such as analogs having chemically modified bases or sugars, backbone modifications, etc. The term "nucleic acid sequence" as used herein can refer to the nucleic acid material itself and is not restricted to the sequence information (i.e., the succession of letters chosen among the five base letters A, G, C, T, or U) that biochemically characterizes a specific nucleic acid, e.g., a DNA or RNA molecule. A nucleic acid sequence is presented in the 5' to 3' direction unless otherwise indicated. The term "nucleic acid segment" is used herein to refer to a nucleic acid sequence that is a portion of a longer nucleic acid sequence.

The terms "open reading frame" and "protein coding region" refer a sequence of several nucleotide triplets which may be translated into a peptide or protein. An open reading frame preferably contains a start codon, i.e., a combination of three subsequent nucleotides coding usually for the amino acid methionine (ATG), at its 5'-end and a subsequent region which usually exhibits a length which is a multiple of 3 nucleotides. An ORF is preferably terminated by a stop-codon (e.g., TAA, TAG, TGA). Typically, this is the only stop-codon of the open reading frame. Thus, an open reading frame in the context of the present invention is preferably a nucleotide sequence, consisting of a number of nucleotides that may be divided by three, which starts with a start codon (e.g., ATG) and which preferably terminates with a stop codon (e.g., TAA, TGA, or TAG). The open reading frame may be isolated or it may be incorporated in a longer nucleic acid sequence, for example in a vector or an mRNA.

The terms "operably linked" and "operably associated" refer to a functional relationship between two nucleic acids, wherein the expression, activity, localization, etc., of one of the sequences is controlled by, directed by, regulated by, modulated by, etc., the other nucleic acid. The two nucleic acids are said to be operably linked or operably associated or in operable association. "Operably linked" or "operably associated" can also refer to a relationship between two polypeptides wherein the expression of one of the polypeptides is controlled by, directed by, regulated by, modulated by, etc., the other polypeptide. Typically a first nucleic acid sequence that is operably linked to a second nucleic acid sequence, or a first polypeptide that is operatively linked to a second polypeptide, is covalently linked, either directly or indirectly, to such a sequence, although any effective three-dimensional association is acceptable. One of ordinary skill in the art will appreciate that multiple nucleic acids, or multiple polypeptides, may be operably linked or associated with one another.

The term "plasmid" refers to a circular nucleic acid vector. Plasmids contain an origin of replication that allows many copies of the plasmid to be produced in a bacterial or eukaryotic cell (e.g., 293T producer cell) without integration of the plasmid into the host cell DNA.

The term "promoter" as used herein refers to a recognition site of a DNA strand to which the RNA polymerase binds. The promoter forms an initiation complex with RNA polymerase to initiate and drive transcriptional activity. The complex can be modified by activating sequences termed "enhancers" or inhibitory sequences termed "silencers".

The term "packaging" refers to the process of sequestering (or packaging) a viral genome inside a protein capsid, whereby a virion particle is formed. This process is also known as encapsidation. As used herein, the term "packaging signal" or "packaging sequence" refers to sequences located within the viral genome which are required for insertion of the viral RNA into the viral capsid or particle.

The term "recombinant" refers to a nucleic acid sequence that comprises portions that do not naturally occur together as part of a single sequence or that have been rearranged relative to a naturally occurring sequence. A recombinant nucleic acid is created by a process that involves the hand of man and/or is generated from a nucleic acid that was created by hand of man (e.g., by one or more cycles of replication, amplification, transcription, etc.). A recombinant virus or viral particle is one that comprises a recombinant nucleic acid. A recombinant cell is one that comprises a recombinant nucleic acid.

The terms "regulatory sequence" and "regulatory element" refer to a nucleic acid sequence that regulates one or more steps in the expression (particularly transcription, but in some cases other events such as splicing or other processing) of nucleic acid sequence(s) with which it is operatively linked. The terms include promoters, enhancers and other transcriptional control elements that direct or enhance transcription of an operatively linked nucleic acid. Regulatory sequences may direct constitutive expression (e.g., expression in most or all cell types under typical physiological conditions in culture or in an organism), cell type specific, lineage specific, or tissue specific expression, and/or regulatable (inducible or repressible) expression.

The term "retinal cell" refers to any of the cell types that comprise the retina, such as retinal ganglion cells, amacrine cells, horizontal cells, bipolar cells, and photoreceptor cells including rods and cones, Muller glial cells, and retinal pigmented epithelium.

An "infectious" virus or viral particle is one that comprises a competently assembled viral capsid and is capable of delivering a polynucleotide component into a cell for which the viral species is tropic. The term does not necessarily imply any replication capacity of the virus. Viral infectivity can be expressed as the ratio of infectious viral particles to total viral particles. Methods of determining the ratio of infectious viral particle to total viral particle are known in the art.

The term "transfection" refers to the introduction of foreign DNA into eukaryotic cells. Transfection may be accomplished by a variety of means known in the art including but not limited to calcium phosphate-DNA co-precipitation, DEAE-dextran-mediated transfection, polybrene-mediated transfection, electroporation, microinjection, liposome fusion, lipofection, protoplast fusion, viral infection, and biolistics.

The term "transduction" refers to the delivery of a gene(s) using a viral vector by means of viral infection. In some embodiments, vectors are transduced by packaging the vectors into virions prior to contact with a cell.

The terms "vector", "expression vector", and "vector construct" refer to a nucleic acid molecule capable of transferring or transporting another passenger DNA or RNA nucleic acid molecule (i.e., a sequence or gene of interest) into a host cell. For instance, either a DNA or RNA vector can be used to derive viral particles. Similarly, a cDNA copy can be made of a viral RNA genome. Alternatively, a cDNA (or viral genomic DNA) moiety can be transcribed in vitro to produce RNA. The transferred nucleic acid (i.e., a sequence or gene of interest) is generally linked to, e.g., inserted into, the vector nucleic acid molecule. A vector may include sequences that direct autonomous replication in a cell, or may include sequences sufficient to allow integration into host cell DNA. The vector is not a wild-type strain of a virus, in as much as it comprises human-made mutations or modifications. Thus, the vector typically is derived from a wild-type viral strain by genetic manipulation (e.g., by addition, deletion, mutation, insertion or other techniques known in the art), as further described herein. Useful vectors include, for example, plasmids (typically DNA plasmids, but RNA plasmids are also of use), phages, cosmids, and viral vectors.

The term "viral vector" refers to either a nucleic acid molecule (e.g., a plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s).

The terms "subject," "patient," "individual," and "host" used interchangeably herein, refer to a mammal, including, but not limited to, murines, felines, simians, humans, mammalian farm animals, mammalian sport animals, and mammalian pets.

The terms "treatment," "treating," and the like, refer to obtaining a desired pharmacologic and/or physiological effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease or at risk of acquiring the disease but has not yet been diagnosed as having it; (b) inhibiting the disease, i.e., arresting its development; and (c) relieving the disease, i.e., causing regression of the disease.

The term 3'-untranslated region (3'UTR) refers to a part of an mRNA or corresponding cDNA, which is located 3' of the protein coding region (i.e., the open reading frame). A 3'UTR is not translated into an amino acid sequence. The 3'UTR sequence is generally encoded by the gene which is transcribed into the respective mRNA during the gene expression process. The genomic sequence is first transcribed into pre-mature mRNA, which comprises optional introns. The pre-mature mRNA is then further processed into mature mRNA in a maturation process. This maturation process comprises the steps of 5'capping, splicing the pre-mature mRNA to excise optional introns and modifications of the 3'-end, such as polyadenylation of the 3'-end of the pre-mature mRNA and optional endo- or exonuclease cleavages etc. The 3'UTR sequence may be an RNA sequence, such as in the mRNA sequence used for defining the 3'UTR sequence, or a DNA sequence which corresponds to such RNA sequence. The term "a 3'UTR of a gene", such as "a 3'UTR of a clarin-1 gene", is the sequence which corresponds to the 3'UTR of the mature mRNA derived from this gene, i.e., the mRNA obtained by transcription of the gene and maturation of the pre-mature mRNA. The term "3'UTR of a gene" encompasses the DNA sequence and the RNA sequence of the 3'UTR.

The term 5'-UTR refers to a particular section of messenger RNA (mRNA) or corresponding cDNA, which is located 5' of the open reading frame of the mRNA. Typically, the 5'-UTR starts with the transcriptional start site and ends one nucleotide before the start codon of the open reading frame. The 5-'UTR may comprise elements for controlling gene expression, also called regulatory elements. The 5'-UTR may be post transcriptionally modified, for example by addition of a 5'-cap. The 5'UTR corresponds to the sequence which extends from a nucleotide located 3' to the 5'-cap, preferably from the nucleotide located immediately 3' to the 5'cap, to a nucleotide located 5' to the start codon of the protein coding region. The nucleotide located immediately 3' to the 5'cap of a mature mRNA typically corresponds to the transcriptional start site. The 5'-UTR sequence may be an RNA sequence, such as in the mRNA sequence used for defining the 5'-UTR sequence, or a DNA sequence which corresponds to such RNA sequence. The term "a 5'UTR of a gene", such as "a 5'UTR of a clarin-1 gene", is the sequence which corresponds to the 5'-UTR of the mature mRNA derived from this gene, i.e., the mRNA obtained by transcription of the gene and maturation of the pre-mature mRNA. The term "5'-UTR of a gene" encompasses the DNA sequence and the RNA sequence of the 5'-UTR.

Embodiments described herein relate to compositions and methods of treating a subject having Usher syndrome III (USH3), and particularly relates to the use of a nucleic acid construct comprising a polynucleotide encoding clarin-1 for the treatment of hearing and/or vision loss associated with USH3, including syndromic hearing and/or loss, where the subject exhibits both hearing and vision loss, and non-syndromic hearing and/or vision loss, where the subject exhibits only vision or hearing loss, but not both.

Usher's syndrome is characterized by deafness and a gradual vision loss. The hearing loss is associated with a defective inner ear, whereas the vision loss is associated with retinitis pigmentosa (RP). Usher's syndrome has three clinical subtypes, known as I, II and III. People with Usher I are born profoundly deaf, and begin to lose their vision in the first decade of life. They also exhibit balance difficulties and learn to walk slowly as children, due to problems in their vestibular system. People with Usher II are not born deaf, but do have hearing loss. They do not seem to have noticeable problems with balance; they also begin to lose their vision later (in the second decade of life) and may preserve some vision even into middle age. People with Usher syndrome III are not born deaf, but experience a gradual loss of their hearing and vision; they may or may not have balance difficulties. The hearing impairment associated with Usher syndrome is better understood and is known to be due to defective sensory cells (aka hair cells) in the cochlea of the inner ear. Hair cells are mechanosensory cells that convert sound vibration to electrical current. These currents are sent to the brain via the auditory nerve, enabling hearing. Defective hair cells results in loss of hearing.

It was found that a cDNA coding sequence of a clarin-1 gene and a 3'UTR nucleic acid that is derived from the 3'UTR of the clarin-1 gene can be provided in a nucleic acid construct, such as a viral vector. The nucleic acid construct can be administered to cells of the inner ear organ to treat hearing loss associated with USH3 or to retinal cells of the eye to treat vision loss associated with USH3. Clarin-1 cDNA without the associated 3'UTR when provided in a nucleic acid construct however failed to treat the hearing loss. Accordingly, compositions for treating hearing loss and/or vision associated with USH3 can include a polynucleotide comprising a nucleic acid sequence that includes a cDNA or mRNA coding sequence of a clarin-1 gene and a 3'UTR nucleic acid that is derived from the 3'UTR of the clarin-1 gene, as well as nucleic acid constructs that include the polynucleotide, and/or vectors that include the polynucleotide. These compositions can be administered to ocular cells (e.g., retinal cells) and/or cells of the inner ear to treat vision and/or hearing loss in a subject in need thereof.

In some embodiments, the nucleic acid coding sequence of the clarin-1 gene can be substantially homologous or have a sequence identity that is substantially identical to native (or nonmutated) clarin-1 mRNA and/or cDNA (i.e., clarin-1 mRNA and/or cDNA not possessing the clarin-1 mutation responsible for USH3) such that when the clarin-1 mRNA and/or cDNA and 3'UTR nucleic acid that is derived from the 3'UTR of the clarin-1 gene are administered to the subject with USH3, vision and/or hearing loss is mitigated. By substantially homologous, it is meant the clarin-1 mRNA and/or cDNA has an at least about 80%, about 90%, about 95%, about 96%, about 97%, about 98%, about 99% or about 100% sequence identity with the nucleotide sequence of the native (or nonmutated) clarin-1 mRNA and/or cDNA.

In some aspects, the isolated polynucleotide can include a cDNA coding sequence of a clarin-1 gene having a sequence identity of wild-type clarin-1 cDNA. For example, the clarin-1 cDNA can have a sequence identity of SEQ ID NO: 3, which corresponds to mouse clarin-1 cDNA, or SEQ ID NO: 4, which corresponds to human clarin-1 cDNA.

In other aspects, the isolated polynucleotide can include fragments of clarin-1 cDNA that can be expressed in ocular cells or cells of the inner ear of a subject with USH3 at an amount effective to treat vision and/or hearing loss associated with USH3.

The 3'UTR nucleic derived from the 3'UTR of a clarin-1 gene refers to a nucleic acid sequence based on the 3'UTR sequence of a clarin-1 gene or on a fragment or part thereof and that can enhance expression of clarin-1 in a cell transfected with a nucleic acid construct, which includes the nucleic acid coding sequence of the clarin-1 gene, compared to a cell transfected with a similar polynucleotide devoid of the 3'UTR nucleic acid. The 3'UTR nucleic can include sequences corresponding to the entire 3'UTR sequence, i.e., the full length 3'UTR sequence of a clarin-1 gene, and sequences corresponding to a fragment of the 3'UTR sequence of a clarin-1 gene.

In some embodiments, the fragment of a 3'UTR of a clarin-1 gene consists of a continuous stretch of nucleotides corresponding to a continuous stretch of nucleotides in the full-length 3'UTR of a clarin-1 gene, which represents at least about 70%, at least about 80%, at least about 90%, at least about 95%, or at least about 99% sequence identity of the full-length 3'UTR of a clarin-1 gene. For example, the 3'UTR nucleic acid can have at least about 70%, at least about 80%, at least about 90%, at least about 95%, or at least about 99% sequence identity to SEQ ID NO: 5 or SEQ ID NO: 6. In other embodiments, the fragment of a 3'UTR of a clarin-1 gene consists of a continuous stretch of nucleotides corresponding to a continuous stretch of nucleotides in the full-length 3'UTR of a clarin-1 gene, which represents at least about 100, at least about 500, at least about 1000, at least about 1500, or at least about 2000 consecutive nucleotides of the full-length 3'UTR of a clarin-1 gene. For example, the 3'UTR nucleic acid can include at least about 100, at least about 500, at least about 1000, at least about 1500, or at least about 2000 consecutive amino acids of SEQ ID NO: 5 or SEQ ID NO: 6.

Such 3'UTR nucleic acids derived from the 3'UTR of the clarin-1 gene including fragments thereof can enhance expression of clarin-1 in a cell transfected with a nucleic acid construct, which includes the nucleic acid coding sequence of the clarin-1 gene by, for example, stabilizing clarin-1 mRNA/cDNA, stabilizing and/or promoting clarin-1 cDNA transcription, stabilizing and/or prolonging clarin-1 production from an mRNA and/or increasing clarin-1 expression or total clarin-1 production from an mRNA/cDNA in a mammalian cell, such as in a human cell. The 3'UTR nucleic acid can stabilize, increase clarin-1 production, and/or prolong clarin-1 production from an mRNA/cDNA in a mammalian cell, such as in a human cell, compared to an mRNA/cDNA comprising a reference 3'UTR or lacking a 3'UTR.

The increased efficiency of the one or more functions exerted by the 3'UTR nucleic acid, such as mRNA/cDNA and/or clarin-1 production stabilizing efficiency and/or the clarin-1 production increasing efficiency, can be at least about 40%, at least about 50%, at least about 60%, at least about 70%, at least about 80%, at least about 90% compared to an mRNA/cDNA comprising a reference 3'UTR or lacking a 3'UTR. The effect of increasing or prolonging clarin-1 production may be determined by (i) measuring clarin-1 amounts, e.g., obtained by expression of a clarin-1 conjugated to a reporter protein, over time. This stabilizing and/or prolonging effect on clarin-1 production can be within a time span of 48 or 72 hours and is at least the amount of clarin-1 produced from a reference nucleic acid molecule lacking a 3'UTR or comprising a reference 3'UTR. Thus, the clarin-1 level observed at a certain time point after initiation of expression, e.g., after transfection, of the nucleic acid construct, for example, 48 or 72 hours post transfection, is preferably higher than the clarin-1 level observed at the same time point after initiation of expression, e.g., after transfection, of a reference nucleic acid molecule comprising a reference 3'UTR or lacking a 3'UTR.

In some embodiments, the polynucleotide may comprise more than one 3'UTR nucleic acid as described above. For example, the polynucleotide may comprise one, two, three, four or more 3'UTR nucleic acids, wherein the individual 3'UTR nucleic acids may be the same or they may be different. For example, the polynucleotide may comprise two essentially identical 3'UTR nucleic acids as described above, e.g., two 3'UTR nucleic acids comprising or consisting of a nucleic acid sequence which is derived from the 3'UTR of a clarin-1 gene or a fragment of the 3'UTR of a clarin-1 gene.

The polynucleotide can further include the 5'-UTR of the clarin-1 gene or be devoid of the 5'-UTR of the clarin-1 gene. The optional 5'-UTR of the clarin-1 gene can be located 5' to the clarin-1 mRNA/cDNA within the polynucleotide or nucleic acid construct describe herein. In some embodiments, the polynucleotide can include clarin-1 cDNA with associated 5'- and 3'UTRs. For example, the isolated polynucleotide can include a nucleic acid sequence having SEQ ID NO: 1 or SEQ 2.

The polynucleotide can be administered to cells through gene therapy using, for example, a nucleic acid construct. In general, there are two approaches to gene therapy in humans. For in vivo gene therapy, a nucleic acid construct encoding the gene or polynucleotide of interest can be administered directly to the patient. Alternatively, in ex vivo gene therapy, cells are removed from the patient and treated with a nucleic acid construct to express the gene of interest. In the ex vivo method of gene therapy, the treated cells are then re-administered to the patient.

Numerous different methods for gene therapy are well known in the art. These methods include, but are not limited to, the use of nucleic acid constructs provided in DNA plasmid vectors as well as DNA and RNA viral vectors. These vectors are engineered to express clarin-1 when integrated into patient cells.

Additionally, nucleic acid constructs for use in methods described herein may have expression signals such as a strong promoter, a strong termination codon, adjustment of the distance between the promoter and the cloned gene, and the insertion of a transcription termination sequence.

In certain aspects, the nucleic acid construct includes a nucleic acid substantially homologous to clarin-1 cDNA and a 3'UTR nucleic acid that is derived from the 3'UTR of the clarin-1 gene operably linked to a promoter to facilitate clarin-1 expression within an ocular cell or cell of the inner ear. The promoter may be a strong, viral promoter that functions in eukaryotic cells such as a promoter derived from cytomegalovirus (CMV), simian virus 40 (SV40), mouse mammary tumor virus (MMTV), Rous sarcoma virus (RSV), or adenovirus. In certain aspects, the promoter is a constitutive CMV promoter.

Alternatively, the promoter used may be tissue-specific, cell type-specific promoter, or a strong general eukaryotic promoter, such as the actin gene promoter. In another aspect, the promoter is a regulated promoter, such as a tetracycline-regulated promoter, expression from which can be regulated by exposure to an exogenous substance (e.g., tetracycline).

The nucleic acid construct may also include sequences in addition to promoters, which enhance expression in the target cells. For example, a nucleic acid substantially homologous to clarin-1 cDNA with associated 3'UTRs can be operably linked to a polyadenylation signal sequence. The polyadenylation signal sequence may be selected from any of a variety of polyadenylation signal sequences known in the art. An exemplary polyadenylation signal sequence is the SV40 early polyadenylation signal sequence. In addition, the nucleic acid construct may also include one or more introns, where appropriate, which can increase levels of expression of the clarin-1.

In some aspects, the nucleic acid construct may include a reporter gene to aid in identification of cells containing and/or expressing the nucleic acid construct provided to the cells. The reporter gene preferably can include a light emitting reporter gene, for example one that encodes a protein that is fluorescent. Accordingly, a reporter gene for use herein can be a green fluorescent protein (GFP) and light emitting derivatives thereof. GFP is from the jellyfish Aquorea victoria and is able to absorb blue light and re-emits an easily detectable green light. GFP may be advantageously used as a reporter because its measurement is simple and reagent free and the protein is non-toxic.

In other aspects, the nucleic acid construct may include a marker to aid in the selection of cells containing the nucleic acid construct. Alternatively, the marker may be co-transfected with the nucleic acid construct. Typically, selectable markers provide for resistance to antibiotics such as but not limited to tetracycline, ampicillin, hygromycin, and neomycin or thymidine kinase.

Introduction of one or more of the nucleic acid construct(s) including clarin-1 cDNA and a 3'UTR nucleic acid that is derived from the 3'UTR of the clarin-1 gene can be achieved using a variety of gene transfer protocols permitting transfection of the polynucleotide or nucleic acid construct into the cells. Genetic change can be accomplished either by incorporation of the new nucleic acid into the genome of the host cell, or by transient or stable maintenance of the new DNA as an episomal element. A cell has been "transfected" when the nucleic acid construct has been introduced inside the cell membrane using any technology used to introduce nucleic acid molecules into cells.

A number of transfection techniques are well known in the art and are disclosed herein. See, for example, Graham et al., Virology, 52: 456 (1973); Sambrook et al., Molecular Cloning, a laboratory Manual, Cold Spring Harbor Laboratories (New York, 1989); Davis et al., Basic Methods in Molecular Biology, Elsevier, 1986; and Chu et al., Gene, 13: 197 (1981). Such techniques can be used to introduce one or more nucleic acid constructs described herein into the cells.

In some aspects, the nucleic acid construct can be introduced into cells of the eye or inner ear using a viral vector. The precise vector and vector formulation used will depend upon several factors, such as the size of the nucleic acid construct to be transferred and the delivery protocol to be used. The nucleic acid construct can also be introduced as infectious particles, e.g., DNA-ligand conjugates, calcium phosphate precipitates, and liposomes.

In general, viral vectors used are composed of a viral particle derived from a naturally occurring virus, which has been genetically altered to render the virus replication-defective and to deliver a recombinant gene of interest for expression in a target cell. Numerous viral vectors are well known in the art, including, for example, retrovirus, adenovirus, adeno-associated virus, herpes simplex virus (HSV), cytomegalovirus (CMV), vaccinia and poliovirus vectors. The viral vector may be selected according to its preferential infection of the cells targeted.

Where a replication-deficient virus is used as the viral vector, the production of infectious virus particles containing either DNA or RNA corresponding to the nucleic acid construct can be achieved by introducing the viral construct into a recombinant cell line, which provides the missing components essential for viral replication. Transformation of the recombinant cell line with the recombinant viral vector will not result in production or substantial production of replication-competent viruses, e.g., by homologous recombination of the viral sequences of the recombinant cell line into the introduced viral vector. Methods for production of replication-deficient viral particles containing a nucleic acid of interest are well known in the art and are described in, for example, Rosenfeld et al., Science 252:431-434, 1991 and Rosenfeld et al., Cell 68:143-155, 1992 (adenovirus); U.S. Pat. No. 5,139,941 (adeno-associated virus); U.S. Pat. No. 4,861,719 (retrovirus); and U.S. Pat. No. 5,356,806 (vaccinia virus).

In some embodiments, the vector can be an adenovirus vector that includes a polynucleotide or nucleic acid construct comprising the clarin-1 cDNA with the associated 3'UTR. Adenoviruses are able to transfect a wide variety of cell types, including non-dividing cells. Any one of more than 50 serotypes of adenoviruses that are known in the art, including the most commonly used serotypes for gene therapy: type 2 and type 5 can be used as the vector. In order to increase the efficacy of gene expression, and prevent the unintended spread of the virus, genetic modifications of adenoviruses have included the deletion of the E1 region, deletion of the E1 region along with deletion of either the E2 or E4 region, or deletion of the entire adenovirus genome except the cis-acting inverted terminal repeats and a packaging signal (Gardlik et al., Med Sci Monit. 11: RA110-121, 2005).

In other embodiments, the vector can be an adeno-associated virus (AAV) vector that includes a polynucleotide comprising the clarin-1 cDNA with the associated 3'UTRs. The AAV vectors can achieve latent infection of a broad range of cell types, exhibiting the desired characteristic of persistent expression of a therapeutic gene in a patient. Any appropriate type of adeno-associated virus known in the art including, but not limited to AAV1, AAV2, AAV3, AAV4, AAV5, AAV6, AAV7, and AAV8 can be used. Previous experiments have shown that genetic modification of the AAV capsid protein can be achieved to direct infection towards a particular tissue type (Lieber, Nature Biotechnology. 21: 1011-1013, 2003). Modified serotype-2 and -8 AAV vectors in which tyrosine residues in the viral envelope have been substituted for alanine residues that cannot be phosphorylated are also contemplated. In the case of tyrosine mutant serotype-2, tyrosine 444 is substitute with alanine (t2 mut 444). In the case of serotype 8, tyrosine 733 is substituted with an alanine reside (t8 mut 733).

In some embodiments, AAV vectors can include those with a mutation of one or more surface-exposed tyrosine residues on capsid proteins. These mutated vectors avoid degradation by the proteasome, and significantly increase the transduction efficiency of these vectors. Mutation of one or more of the tyrosine residues on the outer surface of the capsid proteins including, for example, but not limited to, mutation of Tyr252 to Phe272 (Y252F), Tyr272 to Phe272 (Y272F), Tyr444 to Phe444 (Y444F), Tyr500 to Phe500 (Y500F), Tyr700 to Phe700 (Y700F), Tyr704 to Phe704 (Y704F), Tyr730 to Phe730 (Y730F) and Tyr733 to Phe733 (Y733F) provides improved transduction efficiency of the AAV vectors when compared to wild-type.

In other embodiments, the nucleic acid construct may be introduced into a cell using a non-viral vector. "Non-viral vector" as used herein is meant to include naked DNA (e.g., DNA not contained within a viral particle, and free of a carrier molecules such as lipids), chemical formulations comprising naked nucleic acid (e.g., a formulation of DNA (and/or RNA) and cationic compounds (e.g., dextran sulfate, cationic lipids)), and naked nucleic acid mixed with an adjuvant, such as a viral particle (e.g., the DNA of interest is not contained within the viral particle, but the formulation is composed of both naked DNA and viral particles (e.g., adenovirus particles) (see, e.g., Curiel et al. 1992 Am. J. Respir. Cell Mol. Biol. 6:247-52). Thus, "non-viral vector" can include vectors composed of nucleic acid plus viral particles where the viral particles do not contain the nucleic acid construct within the viral genome.

In some aspects, a liposome non-viral vector can be used to introduce the nucleic acid construct into the cell. Liposomes for use in the method described herein can include a mixture of lipids, which bind to the nucleic acid construct and facilitate delivery of the construct into the cell. Examples of liposomes that can be used include DOPE (dioleyl phosphatidyl ethanol amine), CUDMEDA (N-(5-cholestrum-3-β-ol 3-urethanyl)-N1,N1-dimethylethylene diamine).

The vector used with some embodiments as described herein can be incorporated into pharmaceutical compositions suitable for administration to a subject. In some particular embodiments, the pharmaceutical composition comprises the vectors described herein and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it can be preferable to include isotonic agents, for example, sugars, polyalcohols such as mannitol, sorbitol, or sodium chloride in the composition. Pharmaceutically acceptable carriers can further comprise minor amounts of auxiliary substances, such as wetting or emulsifying agents, preservatives or buffers, which enhance the shelf life or effectiveness of the vector or pharmaceutical composition.

The compositions described herein may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form used depends on the intended mode of administration and therapeutic application. Typical compositions are in the form of injectable or infusible solutions. The typical mode of administration is intratympanic (in the middle ear), intracochlear, intravitreal, parenteral (e.g., intravenous, subcutaneous, intraperitoneal, intramuscular, intrathecal). In one example, the vector can be delivered to a specific location using stereostatic delivery, particularly through the tympanic membrane or mastoid into the middle ear.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the vector in the required amount in an appropriate solvent with one or a combination of ingredients enumerated above, as required, followed by filtered sterilization.

Generally, dispersions are prepared by incorporating the vector into a sterile vehicle that contains a basic dispersion medium and the required other ingredients from those enumerated above. In the case of sterile lyophilized powders for the preparation of sterile injectable solutions, the methods of preparation can include vacuum drying and spray-drying that yields a powder of the active ingredient plus any additional desired ingredient from a previously sterile-filtered solution thereof. The proper fluidity of a solution can be maintained, for example, by the use of a coating, such as lecithin, by the maintenance of the required particle size in the case of dispersion and by the use of surfactants. Prolonged absorption of injectable compositions can be achieved by including an agent in the composition that delays absorption, for example, monostearate salts and gelatin.

The vectors described herein can be administered by a variety of methods known in the art. As will be appreciated by the skilled artisan, the route and/or mode of administration will vary depending upon the desired results. In certain embodiments, the vector may be prepared with a carrier that will protect the vector against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are generally known to those skilled in the art.

The pharmaceutical compositions described herein can include a "therapeutically effective amount" or a "prophylactically effective amount" of the vectors described herein. A "therapeutically effective amount" refers to an amount effective, at dosages and for periods of time necessary, to achieve the desired therapeutic result, in this case for both prophylaxis and treatment of vision loss, hearing loss or impairment of balance without unacceptable toxicity or undesirable side effects.

A therapeutically effective amount of the vector can vary according to factors such as the disease state, age, sex, and weight of the individual, and the ability of the vector to elicit a desired response in the individual. A therapeutically effective amount can also be one in which any toxic or detrimental effects of the vector are outweighed by the therapeutically beneficial effects. A "prophylactically effective amount" refers to an amount effective, at dosages and for periods of time necessary, to achieve the desired prophylactic result. Typically, since a prophylactic dose can be used in subjects prior to or at an earlier stage of disease, the prophylactically effective amount can be less than the therapeutically effective amount.

Dosage regimens can be adjusted to provide the optimum desired response (e.g., a therapeutic or prophylactic response). For example, a single bolus can be administered, several divided doses can be administered over time or the dose can be proportionally reduced or increased as indicated by the exigencies of the therapeutic situation. It can be especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of vector calculated to produce the desired therapeutic effect in association with the required pharmaceutical carrier. The specification for the dosage unit forms can be dictated by and directly dependent on (a) the unique characteristics of the vector and the particular therapeutic or prophylactic effect to be achieved, and (b) the limitations inherent in the art of formulating such vector for treating or preventing vision and/or hearing loss.

In some embodiments, a nucleic acid construct and/or vector comprising a nucleic acid sequence that includes a cDNA coding sequence of a clarin-1 gene and a 3'-UTR nucleic acid that is derived from the 3'-UTR of the clarin-1 gene can be administered to cells of the inner ear organ to treat hearing loss in a subject with USH3. The inner ear organ can include both the hearing and the vestibular organs (including the semicircular canals and the otolith organs (utricle and saccule). These organs have hair cells, which include 1) hearing related sensory cells and supporting cells, including outer hair cells; 2) sensory cells and supporting cells and matrix and mechanical structures for sensing vestibular function (both rotation, linear motion and gravity); and 3) associated neural structures and spiral ganglion cells.

It is known that in the auditory system, three major viral vectors have been investigated for cochlear gene transfection: (1) lentivirus, (2) adenovirus and (3) Adeno-associated virus (AAV). The gene transfected by adenovirus vector has limited expression time and the vector has been associated with adverse immune reactions (Staecker, Brough, Praetorius, & Baker, 2004). The lentivirus vector, although capable of maintaining long term expression, is particularly suited for targeting neurons, but not hair cells (Federico, 1999). Since the AAV vector has several advantages such as long lasting expression of synthesized genes (Cooper et al, 2006), and low risk for pathogenic reactions (because they are artificially manufactured and not ototoxic) (Kaplitt et al., 1994), it can be a preferred viral vector for cochlear protection by gene therapy.

Cochlear gene transfection in animals has utilized several approaches for vector delivery: (1) direct injection through round window membrane (RWM) into the perilymph, (2) intracochlear infusion through cochleostomy, and (3) transfusion through an intact RWM (Aarnisalo, Aarnisalo, Pietola, Wahlfors, & Jero, 2006). The third approach (transfusion through intact RWM) is least invasive and most likely to be accepted in human application.

In other embodiments, a nucleic acid construct and/or vector including a nucleic acid sequence that includes a cDNA coding sequence of a clarin-1 gene and a 3'-UTR nucleic acid that is derived from the 3'-UTR of the clarin-1 gene can be administered to ocular cells to treat vision loss in subject with USH3. In some embodiments the ocular cell can be a retinal cell. The retinal cell can be a photoreceptor, a retinal ganglion cell, a Muller cell, a bipolar cell, an amacrine cell, a horizontal cell, or a retinal pigmented epithelial cell. In some cases, the retinal cell is a photoreceptor cell, e.g., a rod or cone cell.

In some embodiments, a vector, such as AAV vector, which includes clarin-1 cDNA with associated 5'- and 3'UTRs, can be administered to the retinal cells via intraocular injection, by intravitreal injection, subretinal injection or by any other convenient mode or route of administration. Other convenient modes or routes of administration include, e.g., intravenous, intranasal, etc.

In other embodiments, more than one administration (e.g., two, three, four or more administrations) may be employed to achieve the desired level of gene expression over a period of various intervals, e.g., daily, weekly, monthly, yearly, etc.

The compositions and methods of the application will now be described in greater detail in the following non limiting Example.

EXAMPLE

This Example describes the development of a mouse model for progressive hearing loss (PHL) associated USH3, cell types that require Clrn1 for the development and preservation of hearing in mice, the use of AAV-mediated gene therapy to mitigate hearing loss in an USH3 mouse model, and the requirement of 3'UTR of clarin-1 for gene therapy.

Mice

The transgenic mouse founder (TgAC1) was generated in the Case Transgenic and Targeting Facility. The TgAC1 was bred with Clrn1$^{KO/KO}$ mice to generate KO-TgAC1 mice. All protocols described in this report were approved by the Institutional Animal Care and Use Committee (IACUC) at Case Western Reserve University (CWRU) and at University of California San Francisco (UCSF).

Generation of Transgenic Line KO-TgAC1

The aim was to generate Clrn1 homozygous knockout mice (Clrn1$^{-/-}$) that conditionally express wild-type Clrn1 gene in hair cells from embryonic stages and down-regulated postnatally. We generated a construct in which the Atoh1 enhancer (GenBank: AF218258)-β-globin basal promoter (nt 86 to 133 from human β-globin gene; (GenBank: KJ480748) was fused to cDNA representing a full length transcript of mouse Clrn1, including 5' and 3' UTRs (GenBAnk:NM_153385.3). The Atoh1 enhancer element-β-globin basal promoter construct was used previously to achieve hair cell specific expression of target genes. Mice carrying Transgene Atoh1-enhancer-Clarin-1 (TgAC1) are produced by pronuclear microinjection of TgAC1 into wild-type male pronucleus of fertilized eggs from wild-type C57BL/6J (http://ko.cwru.edu/services/transgenics.shtml). The injected transgene integrates into the host genome by non-homologous recombination or random, non-targeted insertion. The endogenous Clrn1 is intact in the founder generation. Eleven TgAC1 founders were obtained from the Case transgenic core facility. TgAC1 mice were bred with Clrn1 mice homozygous for the knockout allele (Clrn1$^{-/-}$) to generate TgAC1; Clrn1+/KO mice (F1 generation). TgAC1; Clrn1$^{+/-}$ mice were bred to generate TgAC1; Clrn1KO/KO mice (F2 generation). The TgAC1; Clrn1$^{-/-}$ mice was designated 'KO-TgAC1'. The genotype of KO-TgAC1 and control sibling mice (carrying at least one wild-type allele of Clrn1) were screened by PCR as described below. Mice from two of the eleven TgAC1 founders restored hearing to Clrn1$^{-/-}$ mice.

Genotype Identification

A PCR-based protocol was used to identify TgAC1 mice. Genomic DNA was isolated as described previously. The primers used for genotyping were 5'-CCCTCTCT-CACACCCCATTA-3' (KA1109) (SEQ ID NO: 7) and 5'-TGAGAACCGGAAAGGCCTTGC-3' (KA1085) (SEQ ID NO: 8). The expected size of the PCR product is 1938 base pairs (bp).

mRNA Expression Analysis

The Clrn1 mRNA expression was detected/amplified using forward primer 5' TTTACCGAAGCCTTTTCTCG 3' (KA893) (SEQ ID NO: 9) and reverse primer 5' GTGGC-CAAAGGAAGTCCATA 3' (KA1061) (SEQ ID NO: 10). The expected PCR products size are 828 bp and 648 bp for WT and KO alleles, respectively. The TgAC1 mRNA was detected/amplified using forward primer 5' CGGCGC-CATGGCATATGAGGCC 3' (KA1138) (SEQ ID NO: 11) to the Atoh1 enhancer element-β-globin basal promoter cassette (upstream of Clrn1 sequence) and the reverse primer 5' GTGGCCAAAGGAAGTCCATA 3' (KA1061) (SEQ ID NO: 10) specific to the Clrn1 3' UTR. The GFP mRNA expression was detected as a 709 bp band using forward primer 5' CAAGGGCGAGGAGCTGTT 3' (KA1203) (SEQ ID NO: 12) and reverse primer 5' CTTGTACAGCTCGTC-CATGC 3' (KA1192) (SEQ ID NO: 13).

Auditory-Evoked Brainstem Response (ABR)

ABRs reflect the electrical responses of both the cochlear ganglion neurons and the nuclei of the central auditory pathway to sound stimulation and ABR thresholds refers to the lowest sound pressure level (SPL) that can generate these electrical responses. To evaluate hearing in KO-TgAC1 mice, ABR to pure tone frequencies, representing the low (8 kHz), mid (16 kHz) and high (32 kHz) frequency range of the cochlea, were recorded. Since Atoh1-enhancer is known to drive expression uniformly in all hair cells in the organ of Corti ABR from 3 characteristic frequencies along the tonotopic gradient of the cochlea should be representative of cochlear function in the KO-TgAC1 mice. Pure tone ABRs were recorded as previously described.

To determine the efficacy of gene therapy in the KO-TgAC1 mice following viral vector delivery (described later), we used an approach that allows us to test function along most of the cochlear turn. Following viral transfection of KO-TgAC1 mice, hearing was evaluated by recording ABRs to broadband click stimuli. Mice were anesthetized by an intraperitoneal injection of ketamine hydrochloride and xylazine hydrochloride. After placing subdermal needle electrodes at the scalp vertex, below the pinna of the left ear (reference), and below the contralateral ear (ground), sounds were presented and ABRs were recorded in free-field conditions as previously described in a sound-proofed chamber. ABR thresholds were determined postoperatively at varying time points, as early as 4 weeks after viral delivery. The lowest stimulus level that yielded a detectable ABR waveform was defined as the threshold, verified both by visual inspection, with complementary computer analysis also defining ABR hearing thresholds for click stimuli.

Scanning Electron Microscopy

Inner ears were excised from the head, and fixed by intra-labyrinthine perfusion with 2.5% glutaraldehyde in 0.1 M sodium cacodylate buffer containing 2 mM CaCl$_2$. They were immersed in the fixative for 2 h and then stored in 1/10th fixative diluted with buffer until collected together for further preparation. The samples were then dissected in buffer and immersed in 1% OSO$_4$ in sodium cacodylatre buffer for 1 h, washed thoroughly and immersed in a saturated aqueous solution of sodium thiocarbohydrazide for 20 min, washed thoroughly and then immersed in 1% OSO$_4$ in sodium cacodylatre buffer for a further 2 h. The thiocarbohydrazide-osmium steps were repeated and the samples then dehydrated in a graded series of ethanols, up to 100% ethanol dried over molecular sieve. They were placed in 100% dry ethanol in a critical point dryer, dried using liquid CO$_2$ as the transitional fluid, and mounted on stubs for insertion into an 54500 cold-field emission scanning electron microscope (FESEM) operated at 5 kV.

Preparation of Recombinant AAV Vectors

The Clrn1 cDNA with its 5' and 3' UTR sequences was 2978 base pairs in length, and comprised a 5'UTR (172 bp), the mouse clarin coding sequence (699 bp), and a large 3' downstream UTR (2107 bp). A construct containing only the above 5' and 3' UTR sequences and a unique NotI site between them was synthesized by GenScript (Piscataway, NJ). This fragment contained flanking XhoI and BamHI restriction sites and was directionally cloned into an AAV vector to generate a parent plasmid devoid of transgene. The Clrn1 coding sequence including 10 nucleotides 5' proximal to the ATG start-codon, or a control hGFP cDNA were inserted via NotI in the above parent construct to generate "smCBA-mClarin(KA)-UTR" and control "smCBA-mCL-UTR-GFP" plasmids, respectively. Transgene expression (mouse clarin-1 or GFP) is driven by the ubiquitous, constitutive smCBA (small chicken β-actin) promoter. The smCBA-mClarin(KA)-UTR and smCBA-mCL-UTR-GFP constructs were separately packaged in the AAV2 capsid serotype or the AAV8(Y733F) capsid tyrosine mutant. All vectors were produced, packaged, and purified according to previously reported methods. Viral vector titers were determined by real-time PCR. Resulting titers for AAV2-smCBA-mClarin(KA)-UTR and AAV8(Y733F)-smCBA-mClarin(KA)-UTR were $8.60 \times 10^{12}$ and $3.41 \times 10^{13}$ vector genomes per milliliter (vg/mL), respectively. Resulting titers for AAV2-smCBA-mCL-UTR-GFP and AAV8 (Y733F)-smCBA-mCL-UTR-GFP were $2.29 \times 10^{12}$ and $2.13 \times 10^{13}$ vg/mL, respectively. A self-complementary AAV8 (Y733F) vector was also generated containing solely the mouse clarin-1 coding sequence with a human influenza hemagglutinin (HA) tag to its 3' termini (smCBA-mClarin-HA). The resulting titer for the scAAV8(Y733F)-smCBA-mClarin-HA vector was $1.23 \times 10^{13}$ vg/mL.

Viral Vector Delivery

AAV 2 or 8 was delivered to the KO-TgAC1 mice cochlea. For gene therapy experiments, mice were used at postnatal day 1-3 (P1-P3) for AAV2 or AAV8 vector delivery to the inner ear through the round window membrane and at P21 and older for auditory testing and cochlea histology. Mice were anesthetized either by hypothermia anesthesia (by placing them on ice for mice younger than P4), or by intraperitoneal injections of ketamine (100 mg/kg) and xylazine (10 mg/kg) (for older mice). Depth of anesthesia was continuously checked by deep tissue response to toe pinch. Body temperature was maintained with a heating pad and monitored with a rectal probe throughout procedures. Animals were closely monitored for signs of distress and abnormal weight loss postoperatively. Mice of either sex were used. All procedures and animal handling complied with NIH ethics guidelines and approved protocol requirements of the IACUC at the CWRU and UCSF.

Surgical Procedures

The procedure for viral micro-injection through the cochlear round window membrane (RWM) was performed on the neonatal mouse. Mice were anesthetized as previously described and a left post-auricular approach was used to expose the tympanic bulla. Subcutaneous tissue dissection with small scissors exposed the post-auricular muscle. After retracting the adipose tissue to the posterior side of the incision, the muscles were separated to the right and left side, perpendicular to the incision, to exposing the otic bulla. The glass micropipette was inserted into the RW through the soft otic bulla, avoiding the stapedial artery. A fixed volume of the viral vector [(2 μl of AAV2-GFP (2.29 $10^{+12}$ vgu/ml) or AAV8-GFP (2.13 $10^{+13}$ vgu/ml) or AAV2-mclarin+3'UTR (8.6 $10^{+12}$ vgu/ml) or AAV8-mclarin+3'UTR (3.4 $10^{+13}$ vgu/ml) or AAV8-mclarin-HA (1.23 $10^{+13}$ vgu/ml)] previously drawn into the glass micropipette, was gently injected through RWM into the scala tympani over 1 min. To allow the vector to spread throughout the cochlear duct, the glass micropipette was left in place for about 1 min after the injection. Because the hole in the RW membrane was extremely small, leakage of perilymph was found to be insignificant after removing the micropipette. The incision was then sealed with connective tissue and mice were kept in an isolated warm cage until they were fully recovered from anesthesia, and were then moved back with the mother.

Whole Mouse Cochlear Epithelium for GFP Imaging

Cochlear epithelium was dissected from P1 or P11 Atoh1-GFP mice and kept in cold PBS for whole mount imaging.

Cochlear Whole Mount Immunofluorescence

Mice cochleae were perfused with 4% PFA in 0.1M PBS (pH 7.4) and incubated in the fixative for 2 hrs at 4° C. The cochleae were subsequently rinsed with PBS three times for 10 min and then decalcified with 5% EDTA in 0.1M PBS. The otic capsule, the lateral wall, tectorial membrane, and Reissner's membrane were removed in that order. The remaining organ of Corti was further dissected for a surface preparation (microdissected into individual turns), then pre-incubated for 1 hr in the blocking buffer containing 0.25% Triton X-100 and 5% normal goat serum. For GFP labeling, the whole mount was then incubated with rabbit anti-GFP antibody (Invitrogen A11122) at 1:250. After an overnight incubation at 4° C., the cochlea turns were rinsed twice for 10 min with PBS and then incubated for 2 hrs in goat anti-rabbit IgG conjugated to Cy2(Jackson ImmunoResearch) diluted to 1:2000 in PBS.

Results

To develop a delayed onset progressive hearing loss model of USH3, we utilized a conditional expression strategy. Briefly, transgenic mice were generated that express Clrn1 under the control of an Atoh1 enhancer, a hair cell-specific regulatory element, in the KO background. The Atoh1 enhancer mediated expression is detectable in mouse cochlear hair cells from embryonic stages to a week after birth. The transgene (TgAC1) consists of a wild-type Clrn1 cDNA sequence fused downstream of the Atoh1 enhancer and β-globin basal promoter regulatory sequences (FIG. 1A). Previous studies on other eukaryotic genes show that UTRs could play crucial roles in posttranscriptional regulation of gene expression by modulating mRNA localization, stability, and translation. We hypothesized that 3' UTR sequence of Clrn1 is a critical non-coding element of the gene and thus included that sequence in the transgene rescue experiment.

Semi-quantitative RT-PCR analysis of mouse cochlear RNA showed that Clrn1 expression derived from TgAC1 is robust at P1 and down regulated postnatally. In contrast, wild-type Clrn1 expression remained stable over time (FIG. 1B). Since specific antibodies to mouse CLRN1 are not available, a mouse harboring an Atoh1-GFP transgene (FIG. 1A) served as a proxy to monitor conditional expression of the mRNA/protein under the control of Atoh1 enhancer. Semi-quantitative RT-PCR analysis of mouse cochlear RNA showed that GFP mRNA expression was robust at P1 but down regulated after P10 (FIG. 1B), a pattern that was mirrored in TgAC1 RT-PCR. At the protein level, GFP expression was robust in inner hair cells (IHCs) and outer hair cells (OHCs) from the apex to the base of the cochlea at P1 and dramatically reduced by P11 (FIG. 1c). These data imply that TgAC1 derived CLRN1 expression is restricted to hair cells in the cochlea and significantly down regulated after P10.

Mice homozygous for the KO allele (Clrn1KO/KO) and carrying the transgene were generated and designated "KO-TgAC1" (FIG. 5). Hearing in the KO-TgAC1 mice (n=10) along with Clrn1KO/KO (KO) (n=10) and control (wild-type, n=5) mice were monitored from P22 to P70 using auditory evoked brainstem response (ABR) thresholds at 8, 16 and 32 kHz. The median ABR threshold in control mice was 30±5 dB SPL (FIG. 1D). At P22, KO mice developed profound hearing loss while most of the KO-TgAC1 mice had ABR thresholds closer to control mice at all frequencies tested. Over the next 40 days, the hearing sensitivity in the KO-TgAC1 mice gradually decreased, reaching a state of profound hearing loss by P70 (ABR threshold >85-90 dB SPL) (FIG. 1D). One-way ANOVA confirmed the statistical significance of these results ($P \leq 0.0001$). Thus: 1) hair cell-specific expression of Clrn1 is sufficient to develop hearing, 2) postnatal expression of Clrn1 is necessary to maintain hearing; and 3) the KO-TgAC1 mice have a variable and progressive hearing loss similar to that reported in USH3 patients.

To investigate the mechanism associated with delayed onset progressive hearing loss in the KO-TgAC1 mice, hair bundle morphology was evaluated using field emission scanning electron microscopy (FESEM) of mid cochlear regions of wild type, KO and KO-TgAC1 mice at P2, P10, P21 and P36. At relatively low magnification, disrupted hair cell bundle was obvious in the KO mice compared to wild type at all ages examined (FIG. 2A). The disarray was more prominent in OHCs than IHCs. Virtually all the OHC bundles appeared disturbed to some degree. In the KO-TgAC1 mice, the OHC and IHC bundles had their morphology restored at all ages examined virtually to the wild type appearance (FIG. 2A). Higher magnification examination primarily of the OHC bundles was also undertaken. In contrast to the KO, the appearance of the OHC bundle morphology and shape of the cuticular plate in KO-TgAC1 was comparable to WT from P2 to P36 (FIG. 2B). However, hair cells from the KO-TgAC1 mice failed to maintain stereocilia with age. The shortest row of stereocilia became depleted by P21 to a greater extent than age-matched control (FIG. 2C). The IHC bundle morphology was similar in both the KO and the KO-TgAC1 mice and showed loss of the shortest one to two rows of stereocilia with age. At P36, loss of the shortest row of stereocilia in the IHC is apparent (FIG. 2B). After P30, bundle structure deteriorated progressively over time in the KO-TgAC1 mice. By P100, only few OHC and IHC bundles remained in the specimens studied and these were severely disrupted (FIG. 2D). These studies show that the hair cell bundle phenotype in the KO-TgAC1 mice is consistent with the delayed onset progressive hearing loss observed in this model and demonstrate postnatal expression of Clrn1 in hair cells is required to maintain hair bundle structure and hearing in adult mice.

We next sought to determine whether a virally-mediated gene therapy approach could prevent or further delay the onset of hearing loss in the KO-TgAC1 model. For these studies, the wild-type Clrn1 gene with or without the 2.5 kb 3' UTR sequence (FIG. 6) was delivered to the cochlea of KO-TgAC1 mice at P1-3 using adeno-associated virus (AAV) 2/8 through the round window membrane. Initially GFP expression was examined at P10 to assess the extent of transfection. At this age, almost all IHCs were GFP positive, whereas a mosaic pattern of GFP positive cells were observed in the three rows of OHCs. Representative specimens from mid-basal turn of the cochlea from two of the five mice inoculated with AAV2/8-GFP are shown in FIG. 3A. Consistent with the literature, AAV2/8 was much more effective at transfecting IHCs as compared to OHCs, though the precise reason behind this variable transfection in hair cells remains unknown.

Subsequently, AAV2/8 containing Clrn1 gene, with or without the 3' UTR was directly injected through the RWM of KO or KO-TgAC1 mice at P1-P3. Functional preservation of hearing was measured using click-evoked ABRs from 4 to 41 weeks after birth. The KO-TgAC1 mice transfected with AAV2/8 Clrn1-3'UTR construct showed significant preservation of structure and function. For example, at P100, un-transfected KO-TgAC1 mice are deaf while KO-TgAC1 mice transfected with Clrn1-3' UTR construct showed ABR thresholds and wave forms (FIG. 3B) and hair bundle structures (FIG. 4) comparable to Clrn1$^{+/+}$ mice. Interestingly, peaks 2, 4 and 5 from the rescued KO-TgAC1 mice show greater amplitudes compared to Clrn1$^{+/+}$ control (FIG. 3b). The reason for this 'gain-of-function' in the rescued KO-TgAC1 mice is not clear, but it is certainly distinguishes wild type from rescued hearing associated with Clrn1. The preservation of the hair cell bundle phenotype provides an anatomical correlate to the rescue of hearing in the transfected KO-TgAC1 mice. The KO-TgAC1 mice transfected with AAV2/8 Clrn1-3' UTR construct (n=3) showed robust and sustained preservation of hearing through adult life compared to KO-TgAC1 mice transfected with Clrn1 without the 3' UTR (n=10) or untransfected KO-TgAC1 mice (n=6) (FIG. 3C).

The 3'UTR of Clrn1 can play a substantial role in post-transcriptional regulation of gene expression, by modulating mRNA localization, stability, and/or translation. The mice with the greatest hearing preservation (n=3) had ABR thresholds close to WT mice (40-50 dB SPL in KO-TgAC1-3' UTR vs 35 dB SPL in WT), with sustained levels for the length of the experiment through 41 weeks (FIG. 3C). One potential reason why ABR thresholds in transfected KO-TgAC1 mice did not reach WT ABR thresholds is likely due to the variable transfection of OHCs. Nevertheless, this data demonstrates that virally-mediated gene transfer can provide robust, long-term preservation of hearing in the delayed onset hearing loss model of USH3.

In summary, virally-mediated gene delivery in a mouse model of USH3 can effectively prevent the onset of deafness associated with a Clrn1 mutation and deliver robust, long-term hearing preservation. These results demonstrate that clarin-1 is well suited as a strategy to prevent deafness in USH3 individuals.

While this application has been particularly shown and described with references to preferred embodiments thereof, it will be understood by those skilled in the art that various changes in form and details may be made therein without departing from the scope of the application encompassed by the appended claims. All patents, publications and references cited in the foregoing specification are herein incorporated by reference in their entirety.

Having described the invention, the following is claimed:

1. A method of slowing the progression of hearing loss in a mammalian subject predisposed or having a progressive hearing loss associated with Usher syndrome III, the method comprising:

administering directly to cells of the inner ear of the subject a therapeutically effective amount of a recombinant adeno-associated viral vector that promotes expression of wild-type clarin-1 in the cells, the vector comprising a wild-type clarin-1 cDNA coding sequence having a 5' end and a 3' end that is flanked at the 5' end with full-length 5'UTR nucleic acid sequence of the clarin-1 gene and at the 3' end with full-length 3'UTR nucleic acid sequence of the clarin-1 gene, wherein the 5'UTR and the 3'UTR nucleic acid sequences enhance expression of clarin-1 in a cell transfected with the vector compared to a cell transfected with a vector that includes a wild-type clarin-1 cDNA coding sequence devoid of the 5'UTR and 3'UTR nucleic acid sequences, and wherein said administering is prior to the onset of hair cell degeneration in said subject.

2. The method of claim 1, the 3'UTR nucleic acid comprising SEQ ID NO: 5.

3. The method of claim 1, the clarin-1 cDNA having the sequence identity of SEQ ID NO: 3 or SEQ ID NO: 4.

4. The method of claim 1, the vector comprising a nucleic acid sequence having the sequence identity of SEQ ID NO: 1 or SEQ ID NO: 2.

* * * * *

SEQUENCE LISTING

<160> NUMBER OF SEQ ID NOS: 13

<210> SEQ ID NO 1
<211> LENGTH: 2978
<212> TYPE: DNA

<213> ORGANISM: Mus musculus

<400> SEQUENCE: 1

| | | | | | |
|---|---|---|---|---|---|
| agtgggtgag | gaaggatgct | tcacggactg | gcgttctgcc | tggtggaacc | actgtaagga | 60 |
| agggcagtgt | ttttcagctg | ctgtgataaa | tgcagccgac | ggggcagtcg | ctacttgatg | 120 |
| ctcacaaagg | tctttgtttt | caagtttgtc | tttaccgaag | cctttctcg | tcatgccaag | 180 |
| ccagcagaag | aagatcatct | tttgcatggc | tggcgtactg | agctttctct | gtgctcttgg | 240 |
| agtggtgaca | gcagtgggca | ccccactgtg | ggttaaagcc | actatcctct | gcaaaacagg | 300 |
| ggctctgctt | gtcaacgcgt | cagggaagga | gctggacaag | ttcatgggcg | agatgcagta | 360 |
| tggcctttc | cacggagaag | gcgtaaggca | atgtgggtta | ggagcaaggc | ctttccggtt | 420 |
| ctcattcttc | ccagatttgg | tccaagccat | ccccgtaagc | atccacatca | atattattct | 480 |
| cttctccatg | attcttgtcg | tcttaaccat | ggtggggaca | gccttcttca | tgtacaatgc | 540 |
| ttttggcaag | ccctttgaaa | ctcttcatgg | accactgggg | ctctatctgg | tcagcttcat | 600 |
| ttcaggctcc | tgtggctgtc | ttgtcatgat | attgtttgcc | tctgaagtga | aagtccaccg | 660 |
| cctttcagag | aaaattgcaa | attttaaaga | agggacctat | gcctacagaa | cacaaaacga | 720 |
| aaactatacc | acctcattct | gggttgtttt | catttgcttt | tttgttcatt | ttttgaatgg | 780 |
| gctcctgata | cgacttgctg | gatttcagtt | ccctttcaca | aaatctaaag | aaacagagac | 840 |
| cactaatgta | gcttcagatt | taatgtactg | aaaagcaaat | atcttcataa | tttctcaata | 900 |
| aggatatgga | cttcctttgg | ccacttttaa | tatgggtgat | ttcatctgtg | catttagact | 960 |
| tcttaagtac | caagccctcc | ttatgttatg | tttacagagc | atgtagtaag | gattcaggct | 1020 |
| ggaaaataac | agaagcagga | ggatggtttc | actgggaaga | cgttcttcct | gatgggtaat | 1080 |
| ggcctgcata | gttagtccaa | agcagttggc | tagatggacg | gatggttact | ccatgtcctt | 1140 |
| actgaccgat | aagatgcacg | ttctcccaag | cagaactcaa | caggcacatg | acatacagtt | 1200 |
| ttgtaagact | ccagggagcc | ttaacttacc | agggacccc | tgagtggacc | acgtggagct | 1260 |
| gggatcaatg | caaaaagcaa | gaggaattta | ttgttccagt | gcactggggt | tgtcccagat | 1320 |
| caacagtgct | ggcagcgacc | cccagcacct | tttcagtgag | ttttatacg | gtttctaggg | 1380 |
| gcagaataga | gcatcagcaa | ctaggcacaa | tatgattgat | ggaacagtgc | acccttaaa | 1440 |
| ctgattggtc | tttaaggaat | gaggtgacaa | ggacttccgt | tgtctgatgg | tggaggtcct | 1500 |
| gtggagtgtg | tccccacaca | caggtcagtt | cctgtccttt | agtctgagaa | atgttaatta | 1560 |
| gcctctccct | tccagagggg | gacgtattcc | atgaccttcc | caaagttctt | gagctgacct | 1620 |
| attcagttaa | ataaaacaga | cgttatttct | aattgtccac | atagtcacag | atcccagaaa | 1680 |
| acagaggtga | aattggtgtc | ttaaactgac | agtgcaccga | atcattgcaa | accttcaagt | 1740 |
| tctttgtaag | tttgcttaga | gcatgatgtc | attatgtctg | gtggtcaaaa | ccagaaaagt | 1800 |
| ttataagcaa | acaagcaagc | tagcaagaaa | ggaagaaaaa | ggaaggaag | aaaggaagaa | 1860 |
| aggaagaaag | gaagaaagga | aggaaggaag | gaaggaagga | aggaaggaag | gaaggaagac | 1920 |
| ggaaagaagc | agatcaatgg | tttctttcct | tatgcatctg | agttcataac | aatggtactt | 1980 |
| acagtggaca | gaatccctac | tagacaagtt | ggtgagagaa | acccactggg | aactgtttcc | 2040 |
| agcttggtgt | ctttggcact | aatgagctcc | aaatcatgaa | aattcagaat | tgaggtggga | 2100 |
| ttgcagtgtg | tcatgggaga | catgaagcat | ggcccaagtc | aaatctttct | ccttgaatta | 2160 |
| ttcaccaaat | gaatctgctg | gagaccagag | gccacaagtg | agcctgaaac | tgacactcct | 2220 |
| taactctcaa | tgtgttaccc | tcaggaaaga | acaaaggaca | aagacattat | ggtgccctgg | 2280 |

```
ccacaaacac cagagatcat agagtttgga aatgctccag aaaaccaatc tggaactagg    2340
aagatggctc agttgataaa gggctgcctc aaaagcttga gagcctgagt tcagattccc    2400
cagcacccat gagaaacgca tgggtttcat acatgtctgt gatcccagca ctgggaaggc    2460
agagctaggc aagtcttaaa gctcaccagc aagccaagtc aaacctaatc agtgcactcc    2520
aaggtcagtg agagaccctg actcaaaaca aaaaaacgga ggtgatggag aaaggcacca    2580
tcagcctcca tgaaccccct catgagcaca cacattttca tttgggaaca atttacatac    2640
aaggaaggag agactgcaca cctgaaatat aaccagctct ggtgatggcc tgctggttac    2700
tctcagacat cagaacatac ttgcttttct caggatggag tcctttcacc ttaattcagg    2760
acactggaag tttctagaag cccaccagct agtctgtcca ggagctggtg catgctttgg    2820
tgatgggcta gtagtgccct gacctggagg tcagacctg  aaattctcaa gcacaaaagg    2880
ctgtgttagg agggaaaggg agggagttga aggctggagg atgaatcccc ctcctctggc    2940
ctccatctac ctctttcctc tctgctcaga ggtctgaa                           2978
```

<210> SEQ ID NO 2
<211> LENGTH: 2352
<212> TYPE: DNA
<213> ORGANISM: Homo sapiens

<400> SEQUENCE: 2

```
tgaaggcagt ttgaaagact tgttttacag attcttagtc caaagatttc caattaggga     60
gaagaagcag cagaaaagga gaaaagccaa gtatgagtga tgatgaggcc ttcatctact    120
gacatttaac ctggcgagaa ccgtcgatgg tgaagttgcc ttttcagctg ggagctgtcc    180
gttcagcttc cgtaataaat gcagtcaaag aggcagtccc ttcccattgc tcacaaaggt    240 cttgttttttg aacctcgccc tcacagaagc cgtttctcat catgccaagc aacagaaga    300 aaatcatttt ttgcatggcc ggagtgttca gttttgcatg tgccctcgga gttgtgacag    360
ccttggggac accgttgtgg atcaaagcca ctgtcctctg caaaacggga gctctgctcg    420
tcaatgcctc agggcaggag ctggacaagt ttatgggtga aatgcagtac gggcttttcc    480
acggagaggg tgtgaggcag tgtgggttgg gagcaaggcc ctttcggttc tcatttttc    540 cagatttgct caaagcaatc ccagtgagca tccacgtcaa tgtcattctc ttctctgcca    600
tccttattgt gttaaccatg gtggggacag ccttcttcat gtacaatgct tttgaaaaac    660
cttttgaaac tctgcatggt cccctagggc tgtacctttt gagcttcatt tcaggctcct    720
gtggctgtct tgtcatgata ttgtttgcct ctgaagtgaa aatccatcac ctctcagaaa    780
aaattgcaaa ttataaagaa gggacttatg tctacaaaac gcaaagtgaa aaatatacca    840
cctcattctg ggtcattttc ttttgctttt tgttcatttt tctgaatggg ctcctaatac    900
gacttgctgg atttcagttc cctttttgcaa aatctaaaga cgcagaaaca actaatgtag    960
ctgcagatct aatgtactga aaggcaaacc tttctataat tttacaaggg agtagacttg   1020
ctttggtcac ttttagatgt ggttaatttt gcatatcctt ttagtctgca tatattaaag   1080
catcaggacc cttcgtgaca atgtttacaa attacgtact aaggatacag gctggaaagt   1140
aagggaagca aaggaaggc tttgaaaagt tgttttatct ggtgggaaat tgcttgaccc    1200
aggtagtcaa aggcagttga ctagaatcga caaattgtta ctccatatat atatatgtgt   1260
gtgtgtgtgt gtgtgtgt   gtgtaagatg tcttcctatc aaaagatat  caaaggcaca   1320 tggaatatat tttaataaaa acaaataata tctctaatat atccacacat tgttgccag    1380
```

| | |
|---|---|
| atttcagaaa actgagctgc aatcgctttc ctaaaacagt agtgtattaa atgaacatct | 1440 |
| ataaaatgta tcaacacaca tttttaaaaaa tttgtttaaa gtatactctt aggccaggcg | 1500 |
| tggtgactca cacctgtaat tccagcactt caggaggcca aggtgggaag atcatttgag | 1560 |
| ttcaggagtt cgagttacag cctgggcaat aaagtgagac cctgtcacta acaaaattaa | 1620 |
| aaaataaaat aaatataaaa tataggcttt aaaaaagcat agtcttatta accatgtctg | 1680 |
| ttggtcaaaa tctgcaaact ctaaaagaag aaaagaagaa aaaaccaagc ttagggtatt | 1740 |
| tttcctcccg tgcctgagtc ccaattacat tcacgacagt actttcaatg aacataattg | 1800 |
| ttaggaccac tgaggaatca tgaaaaatga tctctgctta gtacatttga tgcaaaatga | 1860 |
| cttattaggg gctgttttc tagctatagt gtctcgagta ctaatatgca attatgaaaa | 1920 |
| ttatattaaa tctgggatta tgacggtatc actgtatcat cttggtcttg ttctggctgt | 1980 |
| caccaagcat gacccaggtc aacttttttt ttcccctgaa ttacccatca aattgatctg | 2040 |
| cagctgacta aaggcacag ctgagcctgg aactgaccct tccttcatcc tcaacctgct | 2100 |
| gtcctccaga aagcaccaag gaaaaagcag agaatgacga caaacagatc actaggcctc | 2160 |
| tgaccacagg tgctgagtac tcagcagccc tcatataata ggtttgaaag tactccttaa | 2220 |
| aataaaacac tgtttcccctt tggaactatt tacaaggatg aaacaaccgt atacctgaga | 2280 |
| aataacttgc tctggtgtca attcgctatt cgccagcaga catcagaaca caccgagttt | 2340 |
| ccagatgctg aa | 2352 |

<210> SEQ ID NO 3
<211> LENGTH: 699
<212> TYPE: DNA
<213> ORGANISM: Mus musculus

<400> SEQUENCE: 3

| | |
|---|---|
| atgccaagcc agcagaagaa gatcatcttt tgcatggctg gcgtactgag ctttctctgt | 60 |
| gctcttggag tggtgacagc agtgggcacc ccactgtggg ttaaagccac tatcctctgc | 120 |
| aaaacagggg ctctgcttgt caacgcgtca gggaaggagc tggacaagtt catgggcgag | 180 |
| atgcagtatg ccttttcca cggagaaggc gtaaggcaat gtgggttagg agcaaggcct | 240 |
| ttccggttct cattcttccc agatttggtc caagccatcc ccgtaagcat ccacatcaat | 300 |
| attattctct ctccatgat tcttgtcgtc ttaaccatgg tggggacagc cttcttcatg | 360 |
| tacaatgctt ttggcaagcc ctttgaaact cttcatggac cactggggct ctatctggtc | 420 |
| agcttcattt caggctcctg tggctgtctt gtcatgatat tgtttgcctc tgaagtgaaa | 480 |
| gtccaccgcc tttcagagaa aattgcaaat tttaagaag ggacctatgc ctacagaaca | 540 |
| caaaacgaaa actataccac ctcattctgg gttgttttca tttgcttttt tgttcatttt | 600 |
| ttgaatgggc tcctgatacg acttgctgga tttcagttcc ctttcacaaa atctaaagaa | 660 |
| acagagacca ctaatgtagc ttcagattta atgtactga | 699 |

<210> SEQ ID NO 4
<211> LENGTH: 699
<212> TYPE: DNA
<213> ORGANISM: Homo sapiens

<400> SEQUENCE: 4

| | |
|---|---|
| atgccaagcc aacagaagaa aatcattttt tgcatggccg gagtgttcag ttttgcatgt | 60 |
| gccctcggag ttgtgacagc cttggggaca ccgttgtgga tcaaagccac tgtcctctgc | 120 |
| aaaacgggag ctctgctcgt caatgcctca gggcaggagc tggacaagtt tatgggtgaa | 180 |

| | |
|---|---:|
| atgcagtacg ggcttttcca cggagagggt gtgaggcagt gtgggttggg agcaaggccc | 240 |
| tttcggttct cattttttcc agatttgctc aaagcaatcc cagtgagcat ccacgtcaat | 300 |
| gtcattctct tctctgccat ccttattgtg ttaaccatgg tggggacagc cttcttcatg | 360 |
| tacaatgctt ttggaaaacc ttttgaaact ctgcatggtc ccctagggct gtaccttttg | 420 |
| agcttcattt caggctcctg tggctgtctt gtcatgatat tgtttgcctc tgaagtgaaa | 480 |
| atccatcacc tctcagaaaa aattgcaaat tataaagaag ggacttatgt ctacaaaacg | 540 |
| caaagtgaaa aatataccac ctcattctgg gtcattttct tttgcttttt tgttcatttt | 600 |
| ctgaatgggc tcctaatacg acttgctgga tttcagttcc cttttgcaaa atctaaagac | 660 |
| gcagaaacaa ctaatgtagc tgcagatcta atgtactga | 699 |

```
<210> SEQ ID NO 5
<211> LENGTH: 2107
<212> TYPE: DNA
<213> ORGANISM: Mus musculus

<400> SEQUENCE: 5
```

| | |
|---|---:|
| aaagcaaata tcttcataat ttctcaataa ggatatggac ttcctttggc cacttttaat | 60 |
| atgggtgatt tcatctgtgc atttagactt cttaagtacc aagccctcct tatgttatgt | 120 |
| ttacagagca tgtagtaagg attcaggctg gaaaataaca gaagcaggag gatggtttca | 180 |
| ctgggaagac gttcttcctg atgggtaatg gcctgcatag ttagtccaaa gcagttggct | 240 |
| agatggacgg atggttactc catgtcctta ctgaccgata gatgcacgt tctcccaagc | 300 |
| agaactcaac aggcacatga catacagttt tgtaagactc cagggagcct taacttacca | 360 |
| gggacccct gagtggacca cgtggagctg ggatcaatgc aaaaagcaag aggaatttat | 420 |
| tgttccagtg cactggggtt gtcccagatc aacagtgctg gcagcgaccc ccagcacctt | 480 |
| ttcagtgagt ttttatacgg tttctagggg cagaatagag catcagcaac taggcacaat | 540 |
| atgattgatg gaacagtgca cccttttaaac tgattggtct ttaaggaatg aggtgacaag | 600 |
| gacttccgtt gtctgatggt ggaggtcctg tggagtgtgt ccccacacac aggtcagttc | 660 |
| ctgtccttta gtctgagaaa tgttaattag cctctccctt ccagagggg acgtattcca | 720 |
| tgaccttccc aaagttcttg agctgaccta ttcagttaaa taaaacagac gttatttcta | 780 |
| attgtccaca tagtcacaga tcccagaaaa cagaggtgaa attggtgtct taaactgaca | 840 |
| gtgcaccgaa tcattgcaaa ccttcaagtt cttgtaagt ttgcttagag catgatgtca | 900 |
| ttatgtctgg tggtcaaaac cagaaaagtt tataagcaaa caagcaagct agcaagaaag | 960 |
| gaagaaaaag gaaggaagaa aggaagaaag gaagaaagga agaaaggaa ggaaggaagg | 1020 |
| aaggaaggaa ggaaggaagg aaggaagacg gaaagaagca gatcaatggt ttctttcctt | 1080 |
| atgcatctga gttcataaca atggtactta cagtggacag aatccctact agacaagttg | 1140 |
| gtgagagaaa cccactggga actgttccca gcttggtgtc tttggcacta atgagctcca | 1200 |
| aatcatgaaa attcagaatt gaggtgggat tgcagtgtgt catgggagac atgaagcatg | 1260 |
| gcccaagtca atctttctc cttgaattat tcaccaaatg aatctgctgg agaccagagg | 1320 |
| ccacaagtga gcctgaaact gacactcctt aactctcaat gtgttaccct caggaaagaa | 1380 |
| caaaggacaa agacattatg gtgccctggc cacaaacacc agagatcata gagtttggaa | 1440 |
| atgctccaga aaaccaatct ggaactagga agatggctca gttgataaag gctgcctca | 1500 |
| aaagcttgag agcctgagtt cagattcccc agcacccatg agaaacgcat gggtttcata | 1560 |

| | |
|---|---|
| catgtctgtg atcccagcac tgggaaggca gagctaggca agtcttaaag ctcaccagca | 1620 |
| agccaagtca aacctaatca gtgcactcca aggtcagtga gagaccctga ctcaaaacaa | 1680 |
| aaaaacggag gtgatggaga aaggcaccat cagcctccat gaaccccctc atgagcacac | 1740 |
| acattttcat ttgggaacaa tttacataca aggaaggaga gactgcacac ctgaaatata | 1800 |
| accagctctg gtgatggcct gctggttact ctcagacatc agaacatact tgcttttctc | 1860 |
| aggatggagt cctttcacct taattcagga cactggaagt ttctagaagc ccaccagcta | 1920 |
| gtctgtccag gagctggtgc atgctttggt gatgggctag tagtgccctg acctggaggt | 1980 |
| cagaccctga aattctcaag cacaaaaggc tgtgttagga gggaaaggga gggagttgaa | 2040 |
| ggctggagga tgaatccccc tcctctggcc tccatctacc tctttcctct ctgctcagag | 2100 |
| gtctgaa | 2107 |

```
<210> SEQ ID NO 6
<211> LENGTH: 1372
<212> TYPE: DNA
<213> ORGANISM: Homo sapiens

<400> SEQUENCE: 6
```

| | |
|---|---|
| aaggcaaacc tttctataat tttacaaggg agtagacttg ctttggtcac ttttagatgt | 60 |
| ggttaatttt gcatatcctt ttagtctgca tatattaaag catcaggacc cttcgtgaca | 120 |
| atgtttacaa attacgtact aaggatacag gctgaaagt aagggaagca gaaggaaggc | 180 |
| tttgaaaagt tgttttatct ggtgggaaat tgcttgaccc aggtagtcaa aggcagttga | 240 |
| ctagaatcga caaattgtta ctccatatat atatatgtgt gtgtgtgtgt gtgtgtgtgt | 300 |
| gtgtaagatg tcttcctatc aaaaagatat caaaggcaca tggaatatat tttaataaaa | 360 |
| acaaataata tctctaatat atccacacat ttgttgccag atttcagaaa actgagctgc | 420 |
| aatcgctttc ctaaaacagt agtgtattaa atgaacatct ataaaatgta tcaacacaca | 480 |
| ttttaaaaaa tttgttttaaa gtatactctt aggccaggcg tggtgactca cacctgtaat | 540 |
| tccagcactt caggaggcca aggtgggaag atcatttgag ttcaggagtt cgagttacag | 600 |
| cctgggcaat aaagtgagac cctgtcacta acaaaattaa aaataaaat aaatatcaaa | 660 |
| tataggcttt aaaaaagcat agtcttatta accatgtctg ttggtcaaaa tctgcaaact | 720 |
| ctaaaagaag aaaagaagaa aaaccaagc ttagggtatt tttcctcccg tgcctgagtc | 780 |
| ccaattacat tcacgacagt actttcaatg aacataattg ttaggaccac tgaggaatca | 840 |
| tgaaaatga tctctgctta gtacatttga tgcaaaatga cttattaggg gctgtttttc | 900 |
| tagctatagt gtctcgagta ctaatatgca attatgaaaa ttatattaaa tctgggatta | 960 |
| tgacggtatc actgtatcat cttggtcttg ttctggctgt caccaagcat gacccaggtc | 1020 |
| aacttttttt ttcccctgaa ttacccatca aattgatctg cagctgacta aaggccacag | 1080 |
| ctgagcctgg aactgaccct tccttcatcc tcaacctgct gtcctccaga aagcaccaag | 1140 |
| gaaaaagcag agaatgacag caaacagatc actaggcctc tgaccacagg tgctgagtac | 1200 |
| tcagcagccc tcatataata ggtttgaaag tactccttaa aataaaacac tgtttccctt | 1260 |
| tggaactatt tacaaggatg aaacaaccgt atacctgaga aataacttgc tctggtgtca | 1320 |
| attcgctatt cgccagcaga catcagaaca caccgagttt ccagatgctg aa | 1372 |

```
<210> SEQ ID NO 7
<211> LENGTH: 20
<212> TYPE: DNA
<213> ORGANISM: Artificial Sequence
```

```
<220> FEATURE:
<223> OTHER INFORMATION: Synthetic Construct

<400> SEQUENCE: 7
ccctctctca caccccatta                                               20

<210> SEQ ID NO 8
<211> LENGTH: 21
<212> TYPE: DNA
<213> ORGANISM: Artificial Sequence
<220> FEATURE:
<223> OTHER INFORMATION: Synthetic Construct

<400> SEQUENCE: 8
tgagaaccgg aaaggccttg c                                             21

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
tttaccgaag cctttctctcg                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
gtggccaaag gaagtccata                                               20

<210> SEQ ID NO 11
<211> LENGTH: 22
<212> TYPE: DNA
<213> ORGANISM: Artificial Sequence
<220> FEATURE:
<223> OTHER INFORMATION: Synthetic Construct

<400> SEQUENCE: 11
cggcgccatg gcatatgagg cc                                            22

<210> SEQ ID NO 12
<211> LENGTH: 18
<212> TYPE: DNA
<213> ORGANISM: Artificial Sequence
<220> FEATURE:
<223> OTHER INFORMATION: Synthetic Construct

<400> SEQUENCE: 12
caagggcgag gagctgtt                                                 18

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
cttgtacagc tcgtccatgc                                               20
```